(12) United States Patent
Suh et al.

(10) Patent No.: US 9,259,412 B2
(45) Date of Patent: Feb. 16, 2016

(54) COMPOSITION OF THE TREATMENT OF VASCULAR DISEASES OR KCA3.1 CHANNEL-MEDIATED DISEASES COMPRISING MODAFINIL OR DERIVATIVES THEREOF

(71) Applicant: EWHA UNIVERSITY—INDUSTRY COLLABORATION FOUNDATION, Seoul (KR)

(72) Inventors: Suk Hyo Suh, Goyang-si (KR); Jae Chul Jung, Cheonan-si (KR); Sei Kwan Oh, Seoul (KR)

(73) Assignee: EWHA UNIVERSITY-INDUSTRY COLLABORATION FOUNDATION, Seoul (KR)

( * ) Notice: Subject to any disclaimer, the term of this patent is extended or adjusted under 35 U.S.C. 154(b) by 0 days.

(21) Appl. No.: 14/354,332

(22) PCT Filed: Oct. 24, 2012

(86) PCT No.: PCT/KR2012/008778
§ 371 (c)(1),
(2) Date: Apr. 25, 2014

(87) PCT Pub. No.: WO2013/062316
PCT Pub. Date: May 2, 2013

(65) Prior Publication Data
US 2014/0296333 A1    Oct. 2, 2014

(30) Foreign Application Priority Data

Oct. 25, 2011 (KR) .................. 10-2011-0109292
Oct. 25, 2011 (KR) .................. 10-2011-0109293

(51) Int. Cl.
| | | |
|---|---|---|
| A61K 31/34 | (2006.01) | |
| C07D 307/14 | (2006.01) | |
| C07D 307/52 | (2006.01) | |
| A61K 31/341 | (2006.01) | |
| A61K 31/165 | (2006.01) | |
| A23L 1/30 | (2006.01) | |

(52) U.S. Cl.
CPC .............. *A61K 31/341* (2013.01); *A23L 1/30* (2013.01); *A61K 31/165* (2013.01); *A61K 31/34* (2013.01); *C07D 307/14* (2013.01); *A23V 2002/00* (2013.01)

(58) Field of Classification Search
USPC .................................. 549/494, 496; 514/471
See application file for complete search history.

(56) References Cited

U.S. PATENT DOCUMENTS 5,889,038 A    3/1999    Lencer et al.

FOREIGN PATENT DOCUMENTS

KR    10-1994-0008686 A    5/1994
KR    10-0252390 B1    5/2000

OTHER PUBLICATIONS

Paul A. Rufo et al., "The Antifungal Antibiotic, Clotrimazole, Inhibits Chloride Secretion by Human Intestinal T84 Cells via Blockade of Distinct Basolateral K+ Conductances", Inhibition of T84 K+ Conductance by Clotrimazole, Dec. 1997, vol. 100, No. 12, p. 3111-3120, The American Society for Clinical Investigation, Inc., http://www.jci.org.
Qing Huang et al., "Modafinil modulates GABA-activated currents in rat hippocampal pyramidal neurons", Science Direct, Brain Research, Feb. 29, 2008, vol. 1208, p. 74-78, Elsevier B.V., www.sciencedirect.com.
P. Jenner et al., "Antiparkinsonian and neuroprotective effects of modafinil in the mptp-treated common marmoset", Exp Brain Res, Apr. 6, 2000, vol. 133, p. 178-188, Springer-Verlag.
Fantidis, P., "The Role of Intracellular 35-Cyclic Adenosine Monophosphate (cAMP) in Atherosclerosis," *Current Vascular Pharmacology*, vol. 8, No. 4, 2010, pp. 464-472, 10 pages.
Berg, T., et al., "Increased cAMP Signaling Can Ameliorate the Hypertensive Condition in Spontaneously Hypertensive Rats," *j Vasc Res*, vol. 46, No. 1, Dec. 2009 (published online May 31, 2008), pp. 25-35, 11 pages.
Wang, Z.H., et al., "Blockage of intermediate-conductance-$Ca^{2+}$-activated $K^+$ channels inhibits progression of human endometrial cancer," *Oncogene*, vol. 26, Issue 35, Aug. 2, 2007 (advance online publication Feb. 19, 2007), pp. 5107-5114, 10 pages.
Wulff, H., et al., "K+ Channel Expression during B Cell Differentiation: Implications for Immunomodulation and Autoimmunity," *J Immunol*, vol. 173, No. 2, Jul. 15, 2004, pp. 776-786, 12 pages.

(Continued)

*Primary Examiner* — Andrew D Kosar
*Assistant Examiner* — Raymond Covington
(74) *Attorney, Agent, or Firm* — Masuvalley & Partners

(57) ABSTRACT

The present invention relates to modafinil or derivatives thereof as a medicine for the treatment of vascular diseases or KCa3.1 channel (Ca activated K channel) mediated diseases and a novel use of the same. More specifically, the present invention relates to a pharmaceutical composition for the prevention or treatment of vascular diseases or KCa3.1 channel-mediated diseases comprising modafinil or a derivative of modafinil, or pharmaceutically acceptable salts thereof which relax blood vessels and inhibit KCa3.1 channel currents by increasing intracellular cAMP, a method for treating vascular diseases or KCa3.1 channel-mediated diseases using the composition and a health functional food composition for the prevention or improvement of vascular diseases or the KCa3.1 channel-mediated diseases comprising modafinil or a modafinil derivative compound, or sitologically acceptable salts thereof.

4 Claims, 11 Drawing Sheets

(56) References Cited

OTHER PUBLICATIONS

Jäger, H., et al., "Blockage of Intermediate-Conductance $Ca^{2+}$-Activated $K^+$ channels Inhibit Human Pancreatic Cancer Cell Growth in Vitro," *Molecular Pharmacology*, vol. 65, No. 3, Mar. 1, 2004, pp. 630-638, 9 pages.

Köhler, R., et al., "Blockade of the Intermediate-Conductance Calcium-Activated Potassium Channel as a New Therapeutic Strategy for Restenosis," *Circulation*, vol. 108, No. 9, Sep. 2, 2003, pp. 1119-1125, 8 pages.

Parihar, A.S., et al., "Effects of intermediate-conductance $Ca^{2+}$-activated $K^+$ channel modulators on human prostate cancer cell proliferation," *European Journal of Pharmacology*, vol. 471, Issue 3, Jun. 27, 2003, pp. 157-164, 8 pages.

Rufo, P.A., et al., "The Antifungal Antibiotic, Clotrimazole, Inhibits Chloride Secretion by Human Intestinal T84 Cells via Blockade of Distinct Basolateral $K^+$ Conductances," *J. Clin. Invest.*, vol. 100, No. 12, Dec. 15, 1997, pp. 3111-3120, 10 pages.

Brugnara, C., et al., "Therapy with Oral Clotrimazole Induces Inhibition of the Gardos Channel and Reduction of Erythrocyte Dehydration in Patients with Sickle Cell Disease," *J. Clin. Invest.*, vol. 97, No. 5, Mar. 1, 1996, pp. 1227-1234, 8 pages.

COMPOSITION OF THE TREATMENT OF VASCULAR DISEASES OR KCA3.1 CHANNEL-MEDIATED DISEASES COMPRISING MODAFINIL OR DERIVATIVES THEREOF

This application is a national phase application under 35 U.S.C. §371 of International Application Ser. No. PCT/KR2012/008778 filed on Oct. 24, 2012, and claims the priority under 35 U.S.C. §119 to Korean Patent Application No. 10-2011-0109292, filed on Oct. 25, 2011 and Korean Patent Application No. 10-2011-0109293, filed on Oct. 25, 2011, which are hereby expressly incorporated by reference in their entirety for all purposes.

TECHNICAL FIELD

The present invention relates to modafinil or derivatives thereof as a medicine for the treatment of vascular diseases or KCa3.1 channel (intermediate conductance $Ca^{2+}$-activated $K^+$ channel)-mediated diseases and a novel use of the same. More specifically, the present invention relates to a pharmaceutical composition for the prevention or treatment of vascular diseases or KCa3.1 channel-mediated diseases comprising modafinil or derivatives of modafinil, or pharmaceutically acceptable salts thereof which relax blood vessels and inhibit KCa3.1 currents by increasing intracellular cAMP, a method for treating vascular diseases or KCa3.1 channel-mediated diseases using the composition and a health functional food composition for the prevention or improvement of vascular diseases or the KCa3.1 channel-mediated diseases comprising modafinil or a modafinil derivative compound, or sitologically acceptable salts thereof.

BACKGROUND OF THE INVENTION

Vascular diseases refer to diseases caused by a narrowing of blood vessels and/or increased vascular resistance, and cause insufficient supply of gas and nutrition to tissues because blood flow is interrupted. Causes of Vascular diseases are developed by various causes including inflammation, necrosis, vasospasm and thickening of vessel walls.

The most typical vascular disease is hypertension. Hypertension is the disease with the highest incidence rate among chronic circulatory diseases and approximately 15% of the Korean adult population are estimated to have hypertension. Hypertension refers to a case in which blood pressure is abnormally high, and causes life-threatening complications such as coronary artery diseases, stroke/cerebral infarction, heart failure, and peripheral vascular diseases. Many anti-hypertension medications have been developed to control the increased blood pressure and have different pharmacological actions with different side effects. Since the causes for the increased blood pressure are unknown in about 90% of patients with hypertension, the patients with essential hypertension use multiple medications with different pharmacological actions. Thus, many kinds of anti-hypertensive medications with different pharmacological actions are needed for the patients. Among them, a cAMP-dependent antihypertensive drug is also used, but currently prescribed is just one, iloprost, which is used to treat pulmonary hypertension. However, iloprost is available for an inhaled or intravenous form, but not for an oral form. Thus, it is necessary to develop a new cAMP-dependent hypertension medication which can be used for an oral form, On the other hand, KCa3.1 channel is distributed in nerve cells, erythrocytes, fibroblast, proliferating vascular smooth muscle cells, endothelial cells, immune cells (T cells and B cells), and the like, and contributes to regulation of cell functions in physiological and pathological conditions. [Kaushal V. et al., 2007, J. Neurosci., 27(1):234-244; Anand U. et al., 2006, Neurosci. Lett., 399(1-2):51-56; Wulff H. et al., 2004, J. Immunol., 173(2):776-786; Wulff H. et al., 2007, Curr. Med. Chem., 14(13):1437-1457]. Abnormal (new or increased) KCa3.1 expression might contribute to pathological cellular proliferation and thereby development of various diseases. Thus, KCa3.1 channel is believed to be the target to treat diseases.

Specifically KCa3.1 channel inhibitors are known to inhibit proliferation of immune cells (T cells and B cells), fibroblasts, tumor cells, vascular smooth muscle cells and the like. [Ghanshani S. et al., 2000, J. Biol. Chem., 275(47): 37137-37149; Wulff H. et al., 2004, J. Immunol., 173(2):776-786; Pena T. L. & Rane S. G., 1999, J. Membr. Biol., 172(3): 249-257; Chou C. C. et al., 2008, Expert Rev. Mol. Diagn., 8(2):179-187; Neylon C. B. et al., 2004, Pflugers Arch., 448 (6):613-620]. Therefore, when a drug that inhibits KCa3.1 channel was administered or KCa3.1 channel was destroyed, the proliferation of cancer cells was suppressed and the progression of atherosclerosis, renal fibrosis and post-angioplasty restenosis was inhibited. [Chou C. C. et al., 2008, Expert Rev. Mol. Diagn., 8(2):179-187; Grgic I. et al., 2009, Pflugers Arch., 458(2):291-302; Kohler R. et al., 2003, Circulation, 108(9):1119-1125; Toyama K. et al., 2008, J. Clin. Invest., 118(9):3025-3037]. Further, KCa3.1 channel inhibitors eased the symptoms of autoimmune encephalomyelitis and cardiovascular diseases [Chou C. C. et al., 2008]. Therefore, substances that inhibit KCa3.1 channel are expected to be able to treat various KCa3.1 channel-mediated diseases; however, reports on substances that could effectively inhibit KCa3.1 channel are minimal.

Modafinil is currently being used to treat sleep disorders such as narcolepsy [Ballon J. S. et al., 2006, J. Clin. Psychiatry, 67(4): 554-566], and clinical tests are being performed for use in other psychiatric disorders such as cocaine dependence, attention deficit hyperactivity disorder, depression, seasonal affective disorder, bipolar depression, nicotine addiction, and schizophrenia. [Dackis C. A. et al., 2005, Neuropsychopharmacology, 30(1): 205-211; Donovan J. L. et al., 2003, Ther. Drug Monit., 25(2): 197-202; Minzenberg M. J. et al., 2008, Neuropsychopharmacology, 33(7): 1477-1502; Swanson J. M. et al., 2006, J. Clin. Psychiatry, 67(1): 137-147]. Also, some preclinical evidence indicates the possibility of modafinil use in the treatment of neurodegenerative disease, Parkinson's disease and cancer-related fatigue. [Campos M. P. et al., 2011, Rev. Assoc. Med. Bras., 57(2): 211-219; Portela M. A. et al., 2011, Curr. Opin. Support Palliat. Care, 5(2): 164-168; Wirz S. et al., 2010, Schmerz 24(6): 587-595; Zeng B. Y. et al., 2004, Neurosci. Lett., 354 (1): 6-9]. Since other medications for the treatment have not yet been approved, the use of modafinil for the treatment of these psychiatric disorders is noteworthy.

In this light, because modafinil has been used as a psychostimulant for the treatment of narcolepsy, most of the research about the action mechanism of modafinil has been concentrated on the monoaminergic effect that displays modafinil stimulating histamine, norepinephrine, serotonin, dopamine, and orexin system in brain. Modafinil occupies and regulates the dopamine and norepinephrine transporters. [Madras B. K. et al., 2006, J. Pharmacol. Exp. Ther., 319(2): 561-569; Zolkowska D. et al., 2009, J. Pharmacol. Exp. Ther., 329(2): 738-746]. In addition, modafinil is known to inhibit the vitality of the human liver cytochrome p450 [Robertson P. et al., 2000, Drug Metab. Dispos., 28(6): 664-671] and to function as a neuroprotection [Anronelli T. et al., 1998, Neuroreport, 9(18): 4209-4213; van Vliet S. A. et al., 2008, Brain Res., 1189: 219-228; van Vliet S. A. et al., 2006, Behav. Pharmacol., 17(5-6): 453-462]. On the other hand, modafinil displayed the inhibition of GABA-activated currents [Huang Q. et al., 2008, Brain Res., 1208: 74-78]. However, its main action mechanism is still unclear and more research is needed to explain the effect of modafinil on cells. Furthermore, any use of modafinil for the treatment of vascular diseases or KCa3.1 channel-mediated channel-mediated diseases has not been identified prior to the present invention.

As a result of intensive research efforts to verify the possibility of modafinil as a medicine for treating vascular diseases or KCa3.1 channel-mediated diseases, the present inventors verified that modafinil increases intracellular cAMP levels, and thereby evokes relaxation of vascular smooth muscle, and KCa3.1 current inhibition by the phosphorylation of KCa3.1 channel protein. In addition, the effects to increase intracellular cAMP concentration, and thereby to induce vascular smooth muscle relaxation and KCa3.1 current inhibition have been identified in the novel derivatives thereof, thereby completing the present invention.

SUMMARY OF THE INVENTION

It is an object of the present invention to provide a pharmaceutical composition for the prevention or treatment of vascular diseases comprising modafinil or a derivative of modafinil, or pharmaceutically acceptable salts thereof as active components.

Another object of the present invention is to provide a method for treating vascular diseases comprising administering the composition to an individual.

Another object of the present invention is to provide a health functional food composition for the prevention or improvement of vascular diseases comprising modafinil or a derivative of modafinil compound, or sitologically acceptable salts thereof as active components.

Another object of the present invention is to provide a pharmaceutical composition for the treatment or prevention of KCa3.1 channel-mediated diseases comprising modafinil or a modafinil derivative compound, or pharmaceutically acceptable salts thereof as active components.

Another object of the present invention is to provide a method for treating KCa3.1 channel-mediated diseases comprising administering the composition to an individual.

Still another object of the present invention is to provide a health functional food composition for the prevention or improvement of the KCa3.1 channel-mediated diseases comprising modafinil or a modafinil derivative compound, or sitologically acceptable salts thereof as active components.

Modafinil of the present invention can relax the blood vessels by increasing the intracellular cAMP concentration. In addition, the same effect was found in the newly synthesized derivatives of modafinil. Therefore, modafinil and the newly synthesized derivatives of modafinil of the present invention will be useful as pharmaceutical compositions for the prevention or treatment of vascular diseases through relaxation of the blood vessels by increasing intracellular cAMP, and also as a health functional food. Further, modafinil inhibits the activation of KCa3.1 channels by phosphorylation of the channel protein via increasing the intracellular cAMP level, and KCa3.1 current inhibition was also found in the newly synthesized derivatives of modafinil. Therefore, modafinil and novel derivatives of the present invention may be useful pharmaceutical compositions for the treatment or prevention of diseases including atherosclerosis, cancer, new fibrosis, and postangiplasty restenosis.

BRIEF DESCRIPTION OF THE DRAWINGS

(FIGS. 4A-4C) Current density was obtained at 50 mV during repetitive ramps (upper traces) and current-voltage (I-V) curves obtained at the points marked in upper traces are shown in lower traces. (FIG. 4D) KCa3.1 currents recorded by applying voltage steps (left traces) and the I-V curves of the currents measured at the middle of the voltage steps (right traces). (FIG. 4E) shows the relation ship between the concentration of modafinil and the response. The magnitude of KCa3.1 current inhibition at each treatment was expressed as a percentage of initial KCa3.1 current density at 50 mV (n=7).

(FIGS. 5A and 5B) An effect of the PKA inhibitors H-89(A) and PKI14-22(B) on the inhibitory effects of KCa3.1 currents by modafinil was observed. An inhibitory effect of KCa3.1 currents by modafinil in cells pretreated with H-89 or intracellularly administered with PKI14-22 via micro-pipette was not observed. (FIGS. 5C and 5D) The effect of PKA activator forskolin on KCa3.1 currents (FIG. 5C) and the effect of its PKA inhibitor PKI14-22 (FIG. 5D) were demonstrated. KCa3.1 currents were blocked by forskolin and since they were administered into PKI14-22 cell, the inhibitory effect of forskolin was not observed. These experimental results show that modafinil inhibits KCa3.1 currents by activating PKA like forskolin.

In FIG. 6A, cells which were not exposed to modafinil or forskolin were immunoblotted by anti-KCa3.1 antibody to confirm the presence of KCa3.1 channels (left panel). The arrow indicates the presence of KCa3.1 channels. Cells were pretreated with (or without) the PKA inhibitor H89 for 30 min and then exposed to modafinil or forskolin for 5 min within incomplete media (right panel). Lysates were subjected to immunoblot analysis as indicated. FIG. 6B illustrates summary of modafinil and forskolin-induced phosphorylation of KCa3.1 channels (n=3). Modafinil induced KCa3.1 channel phosphorylation and the effect of modafinil was suppressed by the PKA inhibitor H89. * p<0.05; **p<0.01.

(FIG. 7A) In the membrane patch, single channel currents were activated by 1 µM Ca2+ and 1-EBIO, and the activated currents were abolished by the specific KCa3.1 channel blocker TRAM-34, indicating that the activated single channel currents are the KCa3.1 channel currents. FIGS. 7A and 7B illustrate the effects of the single channel currents and modafinil depending on the holding potentials. In each holding potential, the single channel currents did not change depending on modafinil. FIG. 7C shows the single channel I-V relation under control conditions (●) and after the application of 30 nM modafinil (○). The single channel current was not changed by modafinil. The experimental result shows that applying modafinil directly to the KCa3.1 channel does not regulate the KCa3.1 channel activity.

FIG. 11B shows the relationship between the concentration of iloprost and the reaction (n=7).

DETAILED DESCRIPTION OF INVENTION

Figure 1:
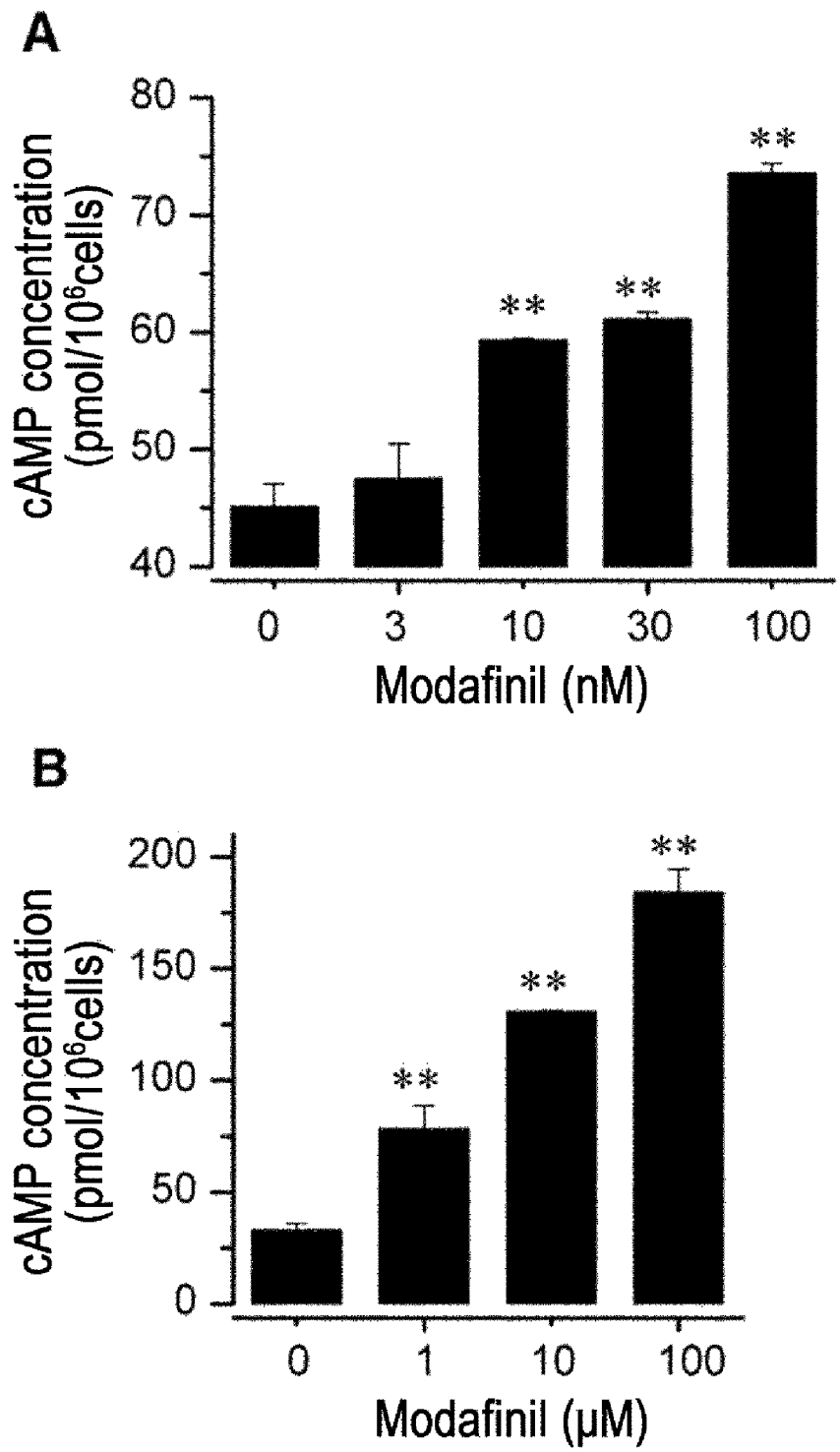
FIG. 1 is a diagram illustrating the effect of modafinil on intracellular cAMP concentration. Modafinil affects intracellular cAMP levels in primary cultured mouse aortic smooth muscle cells. That is, the intracellular cAMP concentration significantly increased from modafinil 10 nM. Cells were treated with modafinil for 3 min within incomplete media. Each point is the mean±standard error of three distinct experiments. **$p<0.01$.

An aspect of the present invention provides modafinil or a modafinil derivative compound pharmaceutical composition for the prevention or treatment of vascular diseases or KCa3.1 channel-mediated diseases comprising modafinil or a modafinil derivative compound, or pharmaceutically acceptable salts as active ingredients.

Modafinil of the present invention is a compound having the structural formula of the following Chemical Formula 1 and is currently being used to treat narcolepsy, and clinical trials for its use in treating other psychiatric disorders are ongoing. Likewise, modafinil is already commercially available as a proven harmless compound and it is apparent that it can be safely used in a pharmaceutical composition for the prevention or treatment of diseases in humans.

[Chemical Formula 1]

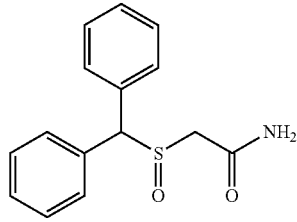

The modafinil is also called 2-(benzhydryl sulfinyl) acetamide. Modafinil that is readily chemically synthesized by a known method by those skilled in the art or prepared as commercially available can be purchased and used.

In addition, a pharmaceutical composition containing the modafinil derivative compound having the structural formula of the following Chemical Formulae 2 to 5 having the same effect of increasing cAMP as modafinil can be provided.

[Chemical Formula 2]

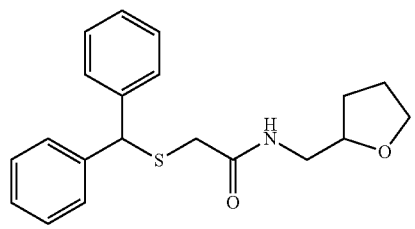

(M006)

[Chemical Formula 3]

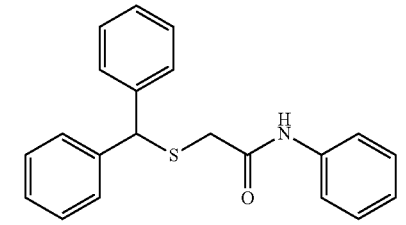

(M008)

[Chemical Formula 4]

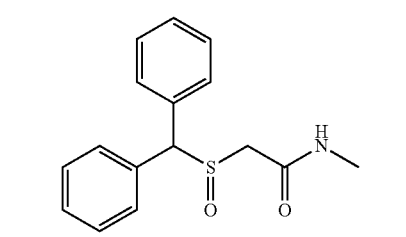

(M015)

[Chemical Formula 5]

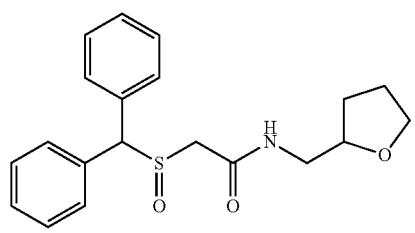

(M020)

The compound of the above Chemical Formula 2 is called 2-(benzhydryl thio)-N-((tetrahydrofuran-2-yl)methyl)acetamide, the above Chemical Formula 3 is called 2-(benzhydryl thio)-N-phenylacetamide, the above Chemical Formula 4 is called 2-(benzhydryl sulfinyl)-N-methylacetamide, and the above Chemical Formula 5 is called 2-(benzhydryl sulfinyl)-N-((tetrahydrofuran-2-yl)methyl) acetamide.

Modafinil derivatives of the above Chemical Formulae 2 to 5 can easily be chemically synthesized according to the following Reaction Formula 1, or can be prepared according to a method known in the art or are commercially available.

[Reaction Formula 1]

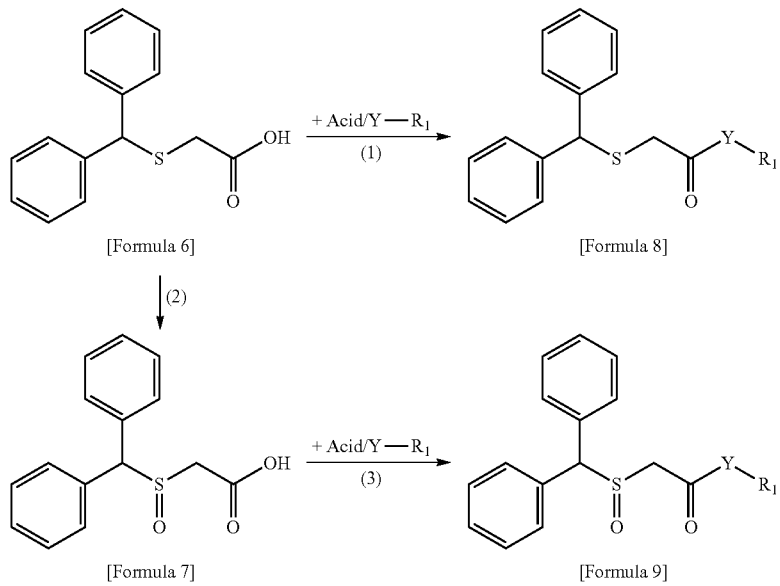

[Formula 6]   [Formula 8]

[Formula 7]   [Formula 9]

Modafinil is well known as a treatment of narcolepsy, however, no report has been made on the ability of modafinil to treat vascular diseases by increasing intracellular cAMP level. Preferably, modafinil or modafinil derivatives having the structural formulae of Chemical Formulae 2 to 5 of the present invention are able to treat vascular diseases by increasing intracellular cAMP levels.

The pharmaceutical composition of the present invention may be used in the form of modafinil of the Chemical Formula 1 or modafinil derivatives of the Chemical Formulae 2 to 5, or pharmaceutically acceptable salts thereof. The phrase "pharmaceutically acceptable salts" of the present invention signifies all the salts that possess a desired biological and/or physiological activity of the compound and that exhibit minimal undesired toxicological effects. Acid addition salt formed by a pharmaceutically acceptable free acid may be useful as a salt. An acid addition salt may be prepared by a conventional method, for example, dissolving the compound in an aqueous solution with an excess amount of acid, and precipitating the salt using a water-miscible organic solvent, such as methanol, ethanol, acetone or acetonitrile.

Acid or alcohol (for example, glycol monomethyl ether) of the compound or water of equimolar amounts may be heated and then the mixture may be dried by evaporation, or the precipitated salts may be filtered using a Buchner funnel. At this moment, an inorganic acid and an organic acid can be used as the free acid, and hydrochloric acid, hydrobromic acid, phosphoric acid, nitric acid, sulfuric acid, tartaric acid and the like may be used as the inorganic acid, and the organic acid includes methane sulfonic acid, p-toluenesulfonic acid, acetic acid, trifluoroacetate, maleic acid, succinic acid, oxalic acid, benzoic acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanilloid acid, hydroiodic acid and the like, but is not limited thereto.

Further, pharmaceutically acceptable metallic salts can be made using a base. Alkali metal or alkali earth metal salts can be acquired by, for example, dissolving the compound in alkali metal hydroxides or alkali earth metal hydroxides of an excess amount and filtering the undissolved compound salts, and then evaporating and drying them. At this time, the metal salts may include in particular sodium, potassium or calcium salt pharmaceutically suitable for the preparation thereof, but is not limited thereto. Also, the corresponding silver salt may be obtained by reacting an alkali metal or alkali earth metal salt with a suitable silver salt (e.g., silver nitrate).

The modafinil of the Chemical Formula 1 or pharmaceutically acceptable salts of modafinil derivative of the Chemical Formulae 2 to 5 may include most of salts of acid or basic groups that can be present in the compound of modafinil or modafinil derivative of the Chemical Formulae 2 to 5. For example, pharmaceutically acceptable salts may include natrium, calcium and potassium salts of a hydroxyl group, and other pharmaceutically acceptable salts of the amino group may include hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) salts, and the salts can be produced by the method of producing salts known in the related art.

The composition of the present invention may be used to prevent or treat the vascular diseases such as hypertension or atherosclerosis. In addition, the vascular diseases that may be treated by the present invention include hypertension, angina, myocardial infarction, coronary artery disease including labile angina, cerebral artery occlusion including stroke, arteriosclerosis, peripheral vascular disease including Buerger's disease, thromboembolism, diabetes foot lesions, venous ulcers, deep vein thrombosis, carotid arteriosclerosis, vasospasm, and arteritis, but are not limited thereto.

Figure 2:
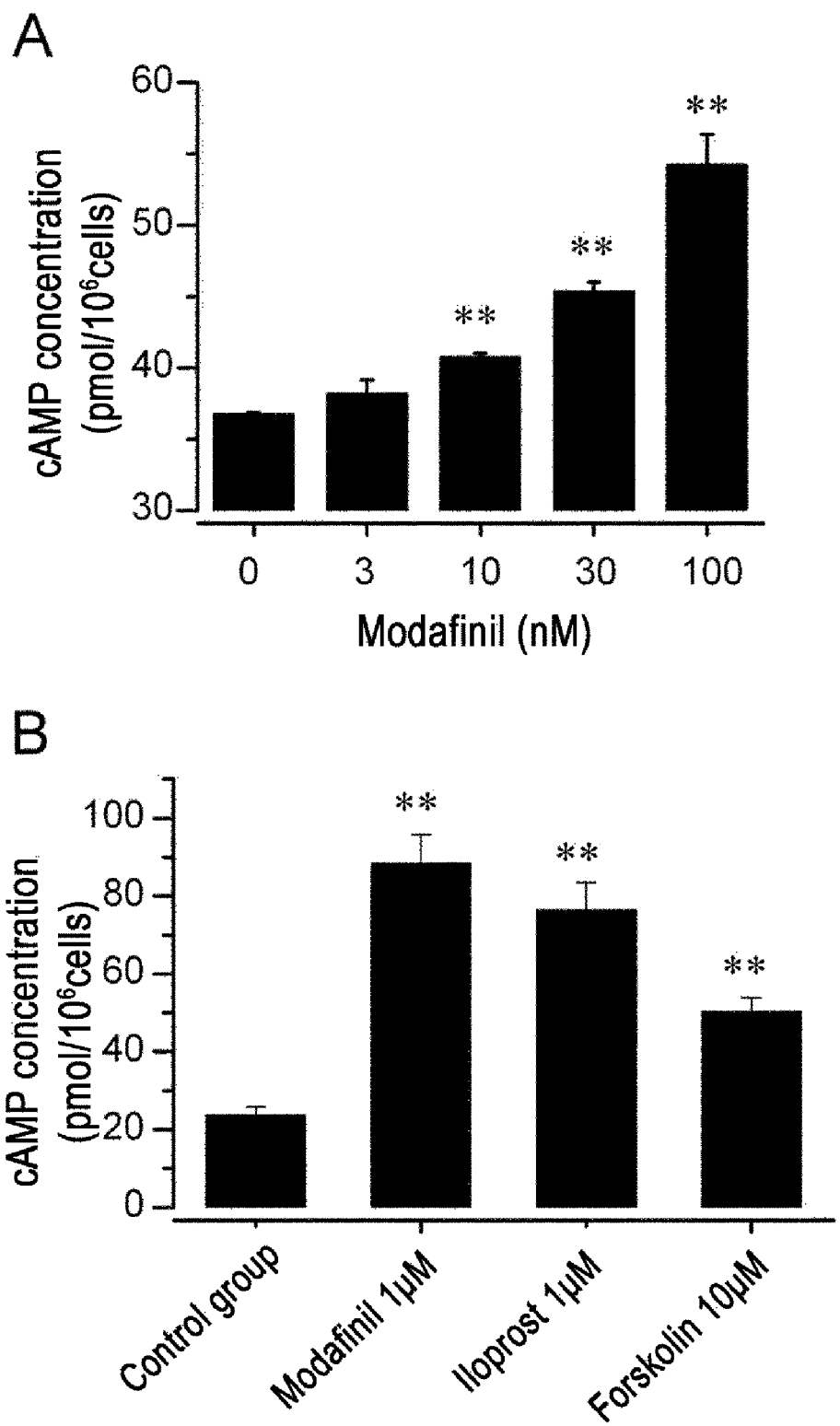
FIG. 2 is a diagram illustrating the effect of modafinil on intracellular cAMP concentration. Modafinil influences the cAMP level in NIH-3T3 cells. That is, modafinil increased the intracellular cAMP concentration in a concentration-dependent manner. Iloprost and forskolin increased cAMP concentration as well, but the corresponding increase by modafinil 1 µM was similar or greater than that of iloprost 1 µM and forskolin 10 µM. Each point is the mean±standard error of three distinct experiments. **$p<0.01$.

One embodiment of the present invention observed that modafinil or modafinil derivatives of Chemical Formulas 2 to 5 of the present invention relax vascular smooth muscles by increasing intracellular cAMP levels (FIGS. 1 and 2). Therefore, modafinil or modafinil derivatives of Chemical Formulae 2 to 5 of the present invention were verified to be able to prevent or treat vascular diseases by increasing intracellular cAMP level, thereby relaxing the vascular smooth muscle.

Therefore, as a feature of the composition of the present invention, the vascular diseases may be treated by increasing intracellular cAMP concentration and relaxing the vascular smooth muscles. In addition, the treatment by increasing intracellular cAMP concentration and relaxing vascular smooth muscles can be performed without any side effect such as elevated blood pressure.

Utilizing the same mechanism as that of the present invention, iloprost is used as a medication to treat pulmonary arterial hypertension by increasing intracellular cAMP to relax blood vessels. However, the modafinil of the present invention has an advantage of having a relatively simpler structure than that of the hypertensive treatment iloprost, and therefore makes the synthesis thereof easier.

The term "prevention" in the present invention means any action which inhibits vascular diseases or delays the onset of the diseases by injecting a pharmaceutical composition according to the present invention, and "treatment" means any action which improves or favourably modifies the symptoms of a vascular disease by injecting the pharmaceutical composition.

Figure 3:
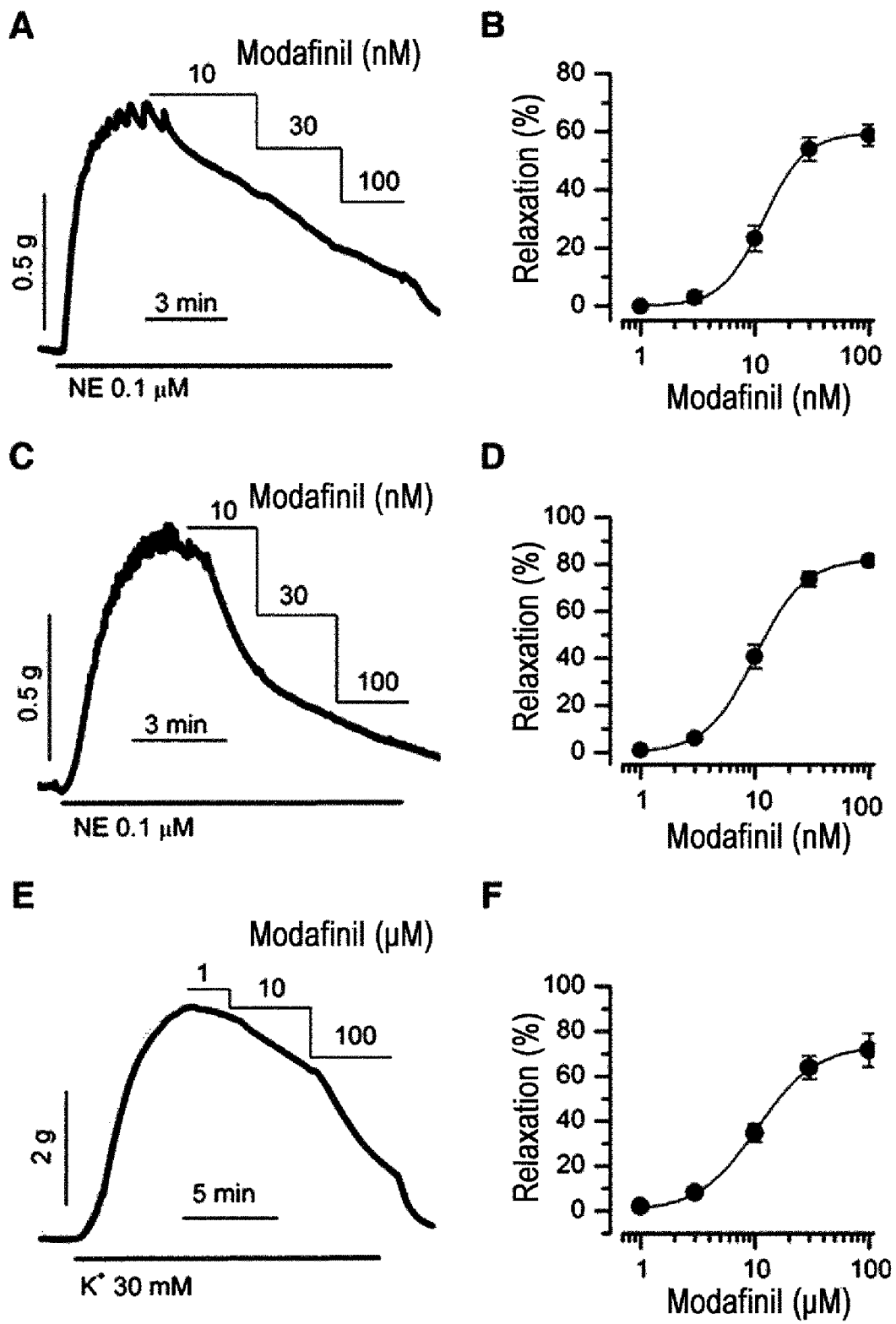
FIG. 3 is a diagram illustrating the effect of modafinil on the concentration-dependent relaxation of vascular smooth muscle. Endothelial cells were removed by gentle rubbing with a cotton ball and nitric oxide production in endothelial cells was inhibited by pretreating with NG-nitro-l-arginine methyl ester (l-NAME). Mouse aortic rings were contracted with 0.1 µM norepinephrine (FIGS. 3A and 3B) and rat pulmonary arterial rings with 0.1 µM norepinephrine (FIGS. 3C and 3D) or 30 mM K+ (FIGS. 3E and 3F). The magnitude of relaxation at each treatment was expressed as a percentage of initial norepinephrine or K+-induced contraction (FIGS. 3B, 3D and 3F, n=4).
Figure 4:
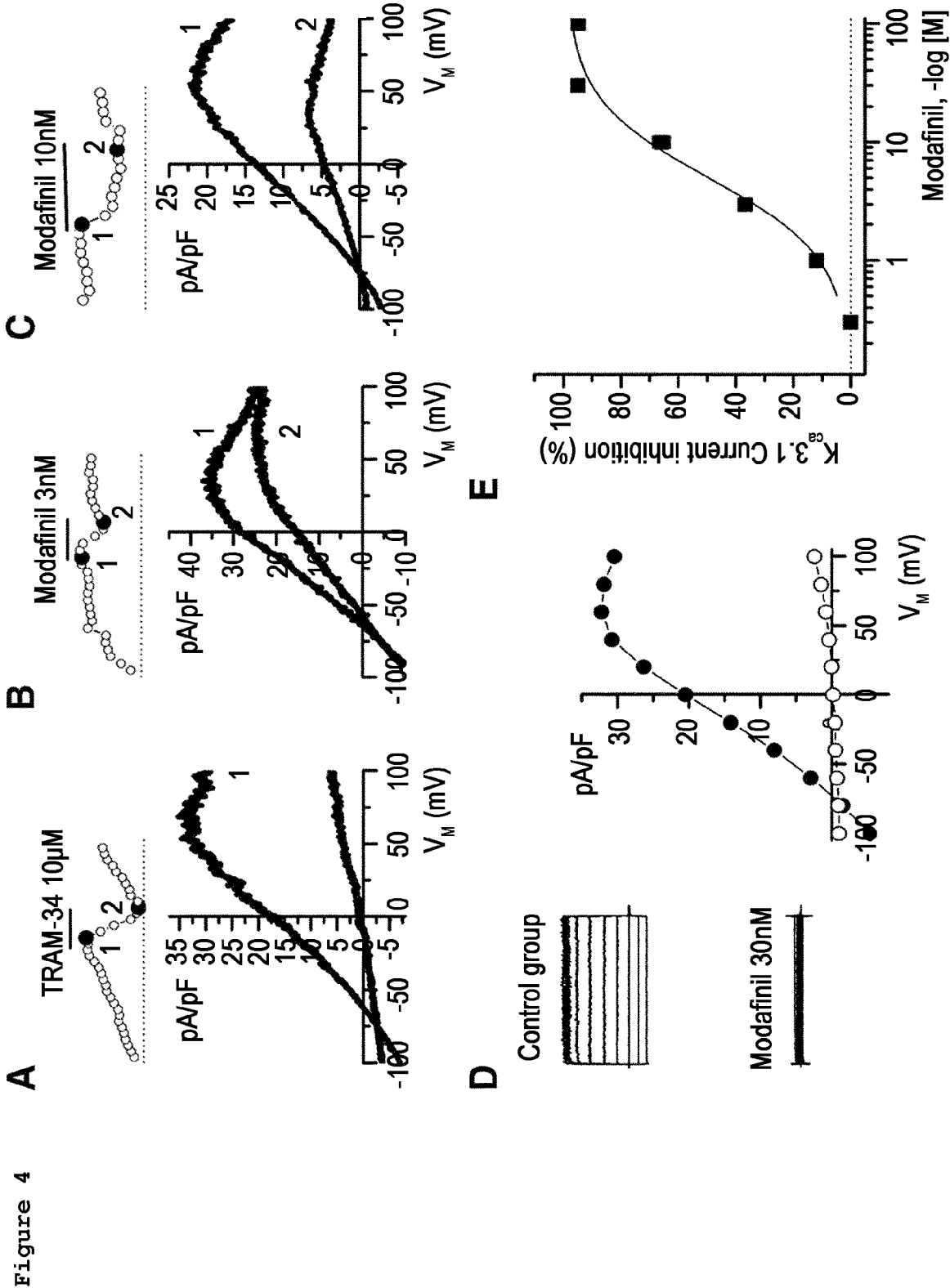
FIG. 4 is a diagram illustrating the effect of modafinil on KCa3.1 currents. KCa3.1 current was activated by loading cells with 1 µM Ca2+ via the glass micro-pipette and applying KCa3.1 channel activator 1-EBIO (100 µM).
Figure 8:
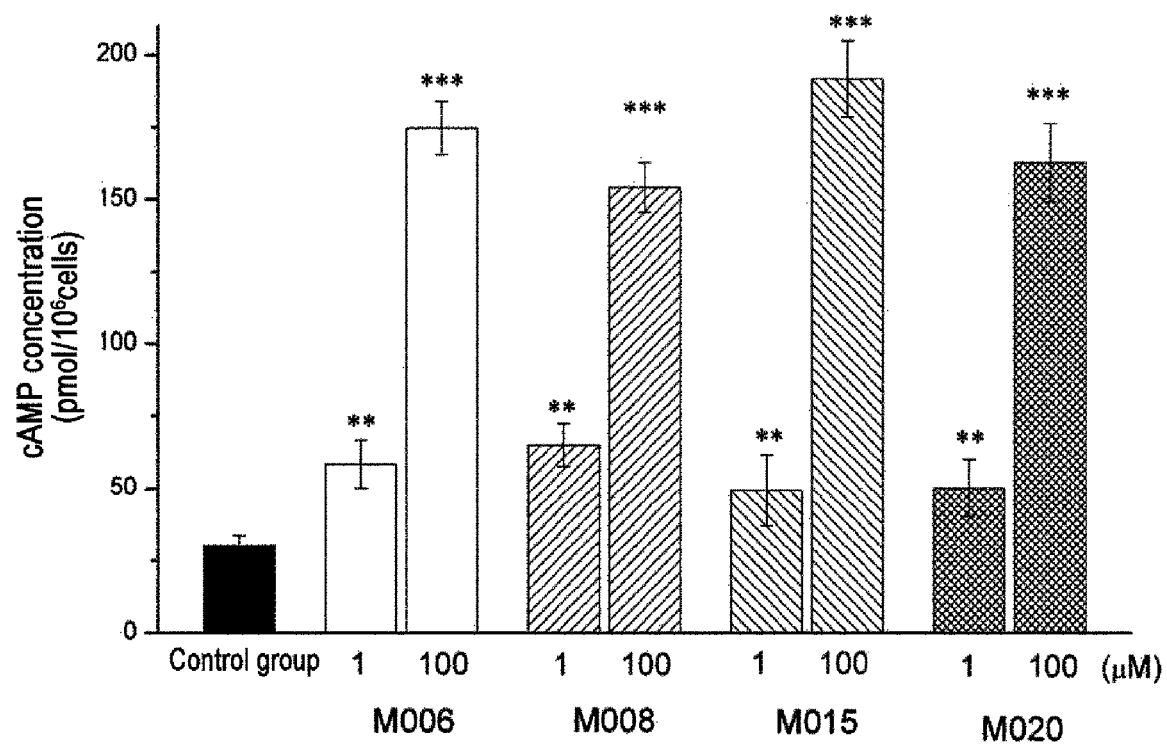
FIG. 8 is a drawing illustrating the effect of modafinil derivatives (M006, M008, M015, M020) on the intracellular cAMP concentration in the cultured NIH-3T3 cell. The derivatives increased the intracellular cAMP concentration in a concentration-dependent manner (n=3).
Figure 9:
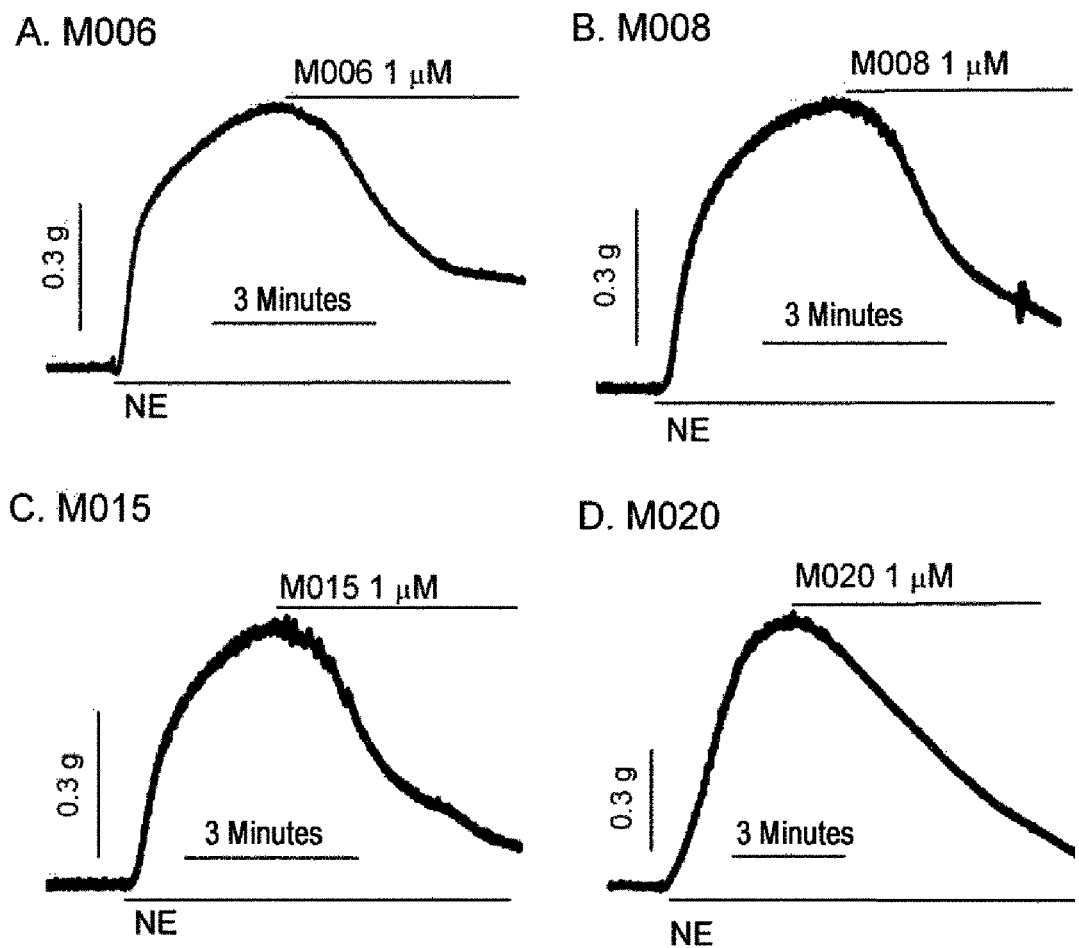
FIG. 9 is a drawing illustrating the effect of modafinil derivatives (M006, M008, M015, M020) on a vascular smooth muscle (VSM) contraction. The derivatives relaxed the norepinephrine (0.1 µM)-induced contraction of rat pulmonary artery. The effect of the derivatives is very similar to that of modafinil.
Figure 11:
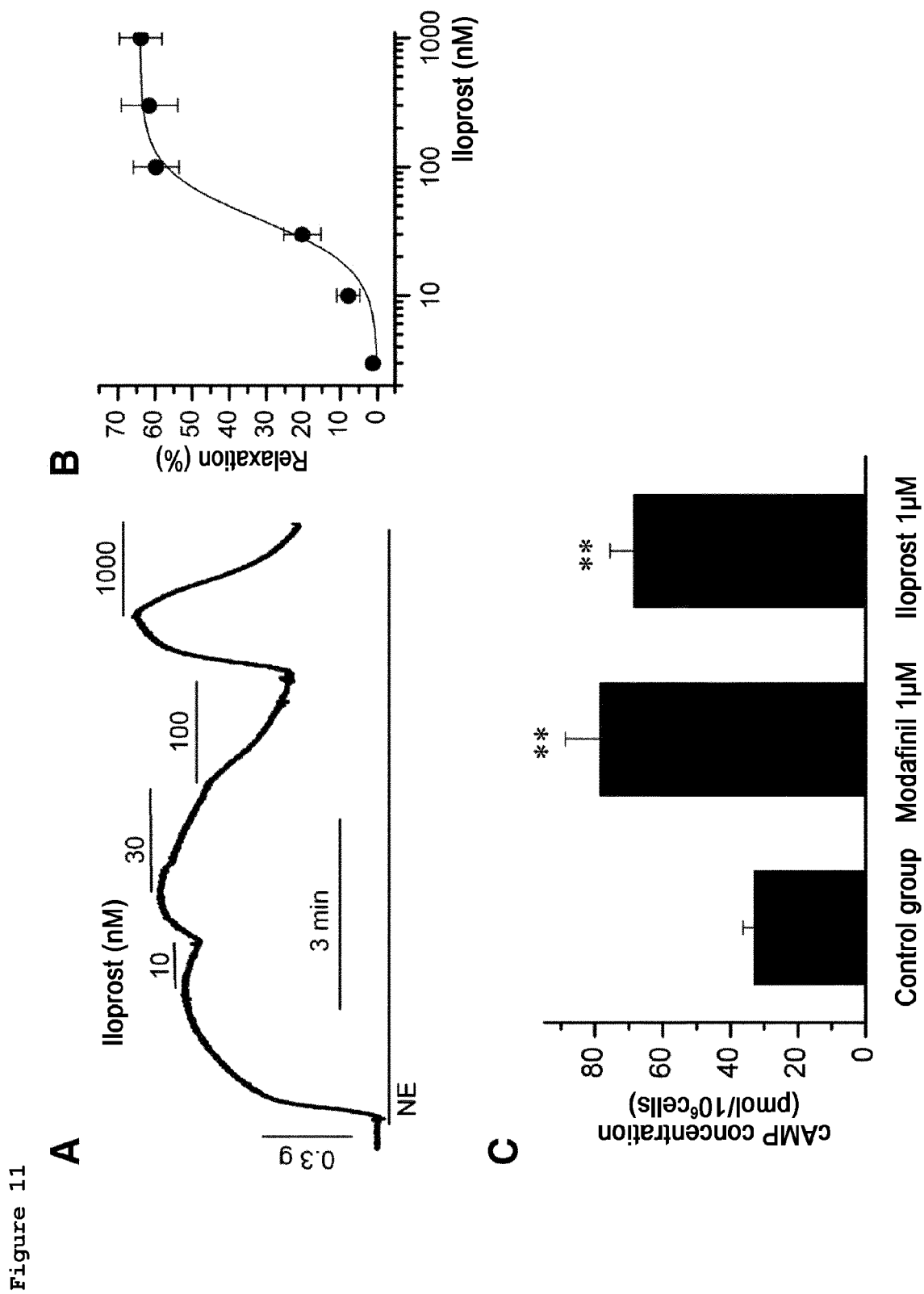
FIG. 11 is a drawing illustrating the effect of iloprost on intracellular cAMP concentration and relaxation of vascular smooth muscle.

Meanwhile, according to the embodiment of the present invention, based on the result of increasing intracellular cAMP concentration (FIG. 1) and relaxing the pre-contracted vascular smooth muscle (FIG. 3) when modafinil is applied, the present inventors have found the action mechanism of modafinil in which increasing intracellular cAMP concentration with modafinil activates a protein kinase A (PKA) and phosphorylates a myosin light chain kinase (MLCK) to relax vascular vessels. They also have found a similar effect compared to that of the existing treatment for hypertension, iloprost (FIG. 11). In addition, they have found that compounds having a structure of Chemical Formulae 2 to 5 also show the same effect as modafinil in increasing intracellular cAMP and relaxing a contracted blood vessel (FIG. 8 and FIG. 9).

The pharmaceutical composition of the present invention may further include pharmaceutically acceptable carriers. The phrase "pharmaceutically acceptable" of the present invention means characteristics of carriers that allow it to be non-toxic when cells or humans is exposed to the composition comprising the carriers. A buffer, preservative, soothing agent, solubilizer, isotonic agent, stabilizer, base, diluting agent, lubricant or others known in the related arts may be used as the carrier without limitation. A carrier, diluting agent and diluent that may be included as pharmaceutical compositions of the present invention may include Lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate and mineral oil.

A filler, extender, binder, humectant, disintegrator, surfactant, diluent or excipient is typically used to formulate a medication. Surfactants typically available to ease the movement of passing through a membrane include derivatives of steroids or cationic lipids or cholesterol hemisuccinates, such as N-[1-(2,3-dioleoyl)propyl-N,N,N-trimethylammonium chloride] (DOTMA).

As another aspect, the present invention provides a method of prevention or treatment of vascular diseases comprising administering the pharmaceutical composition to the individual in need.

In the present invention, the term "individual" means any animals including humans having or capable of having vascular diseases, and the vascular diseases can be effectively prevented or treated by injecting the pharmaceutical composition of the present invention to the individual. The pharmaceutical composition of the present invention can be injected in combination with an existing medication for vascular diseases.

The term "administering" of the present invention means the appropriate method of introducing a predetermined substance to the patient, and the route of administering the composition may be any common route that can reach the aimed tissue. Intraperitoneal injection, intravenous injection, intramuscular injection, subcutaneous injection, intradermal injection, oral injection, topical injection, intranasal injection, intrapulmonary injection, and rectal injection may be performed, but are not limited thereto. Solid medications for oral injections include tablets, pills, powders, granules, capsules, and the like and such solid medications are made by mixing at least one diluting agent in addition to the composition, for example, starch, calcium carbonate, sucrose, lactose or gelatin. Also, in addition to the simple diluting agent, lubricants such as magnesium state and talc are used.

Liquid medications for oral injection include suspensions, solutions, ointments, and syrups, and various diluting agents other than simple diluent materials commonly used such as water and liquid paraffin may include wetting agents, sweeteners, aromatics and preservatives. However, when administered orally, since oral compositions are easily digested, it is preferable to coat or formulate the active medication to prevent decomposition in the stomach. Medications for parenteral administering include sterilized aqueous solutions, non-aqueous solvents, suspensions, ointments, lyophilized medications, and suppositories. Injectable esters such as propylene glycol, polyethylene glycol, vegetable oils such as olive oils, and ethyl oleate may be used for a non-aqueous solvent, suspension. The mechanisms of suppositories include witepsol, macrogol, tween 61. cacao butter, laurin, glyceryl gelatin and the like. In order to increase the stability and water absorption of the compound, carbohydrates such as glucose, sucrose and dextran, antioxidants such as ascorbic acid and glutathione, chelating materials, low molecular weight proteins or other stabilizers may be used.

Also, the pharmaceutical composition of the present invention can be administered into any device through which an active material can be moved to the target cell. The preferable methods of administering and medications are intravenous injection, subcutaneous injection, intradermal injection, intramuscular injection, drip injection, and the like. Parenteral injections can be made using aqueous solutions such as saline, Ringer's solution and the like, and non-aqueous solutions such as vegetable oils, higher fatty acid esters (e.g., oleic acid ethyl etc.), and alcohols (e.g., ethanol, benzyl alcohol, propylene glycol, glycerin, etc.), and can include pharmaceutical carriers including a stabilizer for preventing the change in quality (e.g., ascorbic acid, sodium bisulfite, pyrosulfurous acid, BHA, tocopherol, EDTA, etc.), a emulsifier, a buffer for regulating pH, a preserved agent for checking the development of a microorganism (e.g., phenyl mercury nitrate, chimerosal, benzalconium chloride, phenol, cresol, benzyl alcohol, etc.) and the like.

Meanwhile, the pharmaceutical composition is injected in a pharmaceutically effective dosage. The phrase "pharmaceutically effective amount" refers to the amount sufficient to treat a disease with an acceptable ratio of benefit/risk applicable to medical treatment and not that would not cause any side effects, and the level of effective amount can be readily determined by those skilled in the related arts according to the patient's gender, age, weight, health condition, kind of the disease, severity, activity of the medication, sensitivity to the medication, method of injection, duration of injection, route of injection, and emptying rate, treatment period, combination, or the elements including medication used simultaneously and the elements well known in other medical fields. In general, the active substance can be administered in a dose of about 0.01 mg/kg/day to 1000 mg/kg/day. When administered orally, 50 to 500 mg/kg may be the suitable range, and can be administered more than once per day.

Another aspect of the present invention provides a health functional food composition for the prevention or improvement of vascular diseases comprising modafinil of the Chemical Formula 1 or modafinil derivatives of the Chemical formulae 2 to 5, or sitologically acceptable salts thereof.

When the composition of the present invention is used as a food additive, the modafinil or a derivative thereof can be added intactly, or can be used along with other food or food ingredients, and can be used appropriately according to a conventional method. The amount of active ingredient mixture may be appropriately determined depending on the purpose of use (prevention, health or therapeutic treatment).

The term "health functional food" of the present invention refers to a food whose specific ingredients were produced and processed by a method of extraction, concentration, purification, blending and the like with the object of being a health supplement, and a food whose body modulating functions including bio-defense, regulation of biological rhythms, prevention of diseases and recovery therefrom, are designed and processed to be able to be demonstrated by the ingredients. The health food composition may perform the functions related to the prevention of diseases and the recovery therefrom.

Further, the kinds of health food for which the composition of the present invention can be used are not limited. In addition, the compositions of the present invention including modafinil, or derivatives thereof as the active ingredients may be prepared by mixing other ingredients and the known additives that can be contained in health functional food depending on the choice of those skilled in the related arts. Examples of food that can be added include meat, sausage, bread, chocolates, candies, snacks, confectionery, pizza, ramen, other noodles, gums, dairy products including ice cream, various soups, beverages, tea, drinks, alcoholic beverages, vitamin complexes and the like, and can be prepared by adding to juice, tea, jelly and the like whose main ingredients are the compounds of the present invention.

Another aspect of the present invention provides modafinil or a modafinil derivative compound pharmaceutical compositions for the treatment or prevention of KCa3.1 channel-mediated diseases comprising modafinil or a modafinil derivative compound, or pharmaceutically acceptable salts thereof as active ingredients.

The modafinil and derivatives thereof are as described above. No report has been made about the ability of modafinil, a well-known treatment for narcolepsy, to treat KCa3.1 channel-mediated diseases by inhibiting KCa3.1 channel currents through KCa3.1 channel phosphorylation by increasing intracellular cAMP levels. Preferably, modafinil or modafinil derivatives having the structural formula of the Chemical Formulae 2 to 5 of the present invention increase intracellular cAMP level and inhibit KCa3.1 channel currents through KCa3.1 channel phosphorylation, and therefore, treat KCa3.1 channel-mediated diseases related to KCa3.1 channel activities.

The pharmaceutical composition of the present invention may be used in the form of modafinil, derivatives thereof, or pharmaceutically acceptable salts thereof. The definitions and types of pharmaceutically acceptable salts are as described above.

The composition of the present invention may be used without any limitation to prevent or treat KCa3.1 channel-mediated diseases. The term "KCa3.1 channel-mediated disease" in the present invention refers to any disease regulated by the activity of KCa3.1 channel which is distributed to red blood cells, immune cells, proliferating vascular smooth muscle cells, endothelial cells, some parts of tumor cells, secreting epithelial cells and the like. Since KCa3.1 channel is generally distributed to various cells as the above and is relatively safe, the medications that regulate KCa3.1 channels can be used as the prevention or treatment of various diseases.

Therefore, examples of KCa3.1 channel-mediated diseases that can be treated due to the present invention include sickle cell anemia; immune diseases such as acute immune responses and auto-immune diseases; vascular diseases such as restenosis and atherosclerosis; brain disorders such as traumatic brain injury, cerebral ischemia, and neurodegenerative diseases; cancers such as prostate cancer and pancreatic cancer; or secretory diarrhea, but are not limited thereto.

Many studies have already been conducted on KCa3.1 channel inhibitors. The prevention of red blood cell dehydration in sickle-cell anemia by KCa3.1 channel inhibitors has been shown [Brugnara, C. et al., 2001, Drug News Perspect., 14:208; De Franceschi, L. et al., 1994, J. Clin. Invest., 93:1670; Brugnara, C. et al., 1996, J. Clin. Invest., 97:1227] and, KCa3.1 inhibitor, ICA-17043, is under clinical studies in combination with hydroxylurea [Swerdlow, P. et al., 2006, Blood, 108:Abstract 685]. Therefore, it is apparent that KCa3.1 channel inhibitor of the present invention may be used to prevent or treat sickle cell anemia. Inhibitory effect of calcium ion signal of all T cells of KCa3.1 channel inhibitor [Ghanshani, S. et al., 2000, J. Biol. Chem., 275:37137; Jensen, B. S. et al., 1999, Proc. Natl. Acad. Sci. USA, 96:10917], central memory T cell inhibitory effect [Chandy, K. G. et al., 2004, Trends Pharmacol. Sci., 25:280; Wulff, H. et al., 2003, J. Clin. Invest., 111:1703; Vennekamp, J. et al., 2004, Mol. Pharmacol., 65:1364], acute immune response inhibitory effect [Wulff, H. et al., 2004, J. Immunol., 173:776; Wulff, H. et al., 2000, Proc. Natl. Acad. Sci. USA, 97:8151], and example of being used for the treatment of autoimmune disease [Khanna, R. et al., 2001, Am. J. Physiol. Cell Physiol., 280:C796; Chung, I. et al., 2002, J. Neuroimmunol., 122:40] of KCa3.1 channel inhibitor have been shown. Therefore, it is apparent that KCa3.1 channel inhibitor of the present invention may be used to prevent or treat autoimmune diseases.

Also, the inhibitory effect of KCa3.1 channel inhibitor on proliferation of vascular smooth muscle cells and fibroblasts has been shown [Kohler, R. et al., 2003, Circulation, 108: 1119; Pena, T. L. et al., 2000, J. Biol. Chem., 275:13677; Neylon, C. B., 2002 Vasc. Pharmacol., 38:35; Tharp, D. L. et al., 2006, Am. J. Physiol. Heart Circ. Physiol., 291:H2493], and the fact that KCa3.1 channel plays an important role on revascularization in heart after ischemia has been found [Saito, T. et al., 2002, Clin. Exp. Pharmacol. Physiol., 29:324]. Therefore, it is apparent that KCa3.1 channel inhibitor of the present invention may be used for prevention or treatment of vascular disease. In addition, it was shown that KCa3.1 channel inhibitor may reduce a brain edema and intracranial pressure that occur after an acute subdural hematoma caused by a shock [Mauler, F. et al., 2004, Eur. J. Neurosci., 20:1761] and that it can also reduce neuronal cell death by reducing oxidative burst in microglia [Khanna, R. et al., 2001, Am. J. Physiol. Cell Physiol., 280:C796; Kaushal, V. et al., 2007, J. Neurosci., 27:234]. Therefore, it is apparent that KCa3.1 channel inhibitor of the present invention can be used for the prevention or treatment of brain disorders.

It was also shown that KCa3.1 channel inhibitor inhibits proliferation of prostate cancer cell lines [Parihar, A. S. et al., 2003, Eur. J. Pharmacol., 471:157], and pancreatic cancer cell lines [Jager, H. et al., 2004, S. Mol. Pharma, 65:630], and since it inhibits angiogenesis [Grgic, I. et al., 2005, Arterioscler. Thromb. Vasc. Biol., 25:704], it can also be used as a medication that inhibits angiogenesis of tumor. Thus, it is apparent that KCa3.1 channel inhibitor of the present invention may be used in the prevention or treatment of cancer. Lastly, KCa3.1 channel inhibitor was shown to inhibit secretory diarrhea by inhibiting secretion of intestinal epithelial cells due to cholera toxin [Rufo, P. A. et al., 1997, J. Clin. Invest., 100:3111; Lencer, W. I. et al., 1996, U.S. Pat. No. 5,889,038]. Therefore, it is also apparent that KCa3.1 channel inhibitor of the present invention may be used in the prevention or treatment of secretory diarrhea.

According to one embodiment of the present invention, it was verified that modafinil or modafinil derivatives of Chemical Formulae 2 to 5 of the present invention increase intracellular cAMP, phosphorylates KCa3.1 channel, and inhibits KCa3.1 currents (FIG. 2 and FIGS. 4 to 7). Therefore, modafinil or modafinil derivatives of Chemical Formulae 2 to 5 of the present invention inhibit KCa3.1 channel and thus, it was verified to have a possibility of treating immune diseases, vascular diseases, cerebral diseases, cancers, secretory diarrhea and the like.

Therefore, the composition of the present invention can treat the KCa3.1 channel-mediated diseases by the feature of inhibiting KCa3.1 channel by increasing intracellular cAMP concentration.

The same mechanism as the present invention, that is, medications that inhibit KCa3.1 channel directly include a medication like TRAM-34. In case of inhibiting KCa3.1 channel directly, the function of the vascular endothelial cell is inhibited so the contractibility of the blood vessel increases and the blood pressure increases. However, since modafinil of the present invention relaxes vascular smooth muscle by increasing cAMP, there is an advantage in that the same treatment effect can be obtained as the above without much increase in blood pressure compared to the inhibitor of KCa3.1 channel.

The term "prevention" in the present invention means any action which inhibits KCa3.1 channel-mediated diseases or delays the onset of the diseases by administering a pharmaceutical composition according to the present invention, and "treatment" means any action that improves or favourably modifies the symptoms of diseases such as an atherosclerosis, cancer, renal fibrosis, postangiplasty restenosis and the like by administering the pharmaceutical composition.

Figure 5:
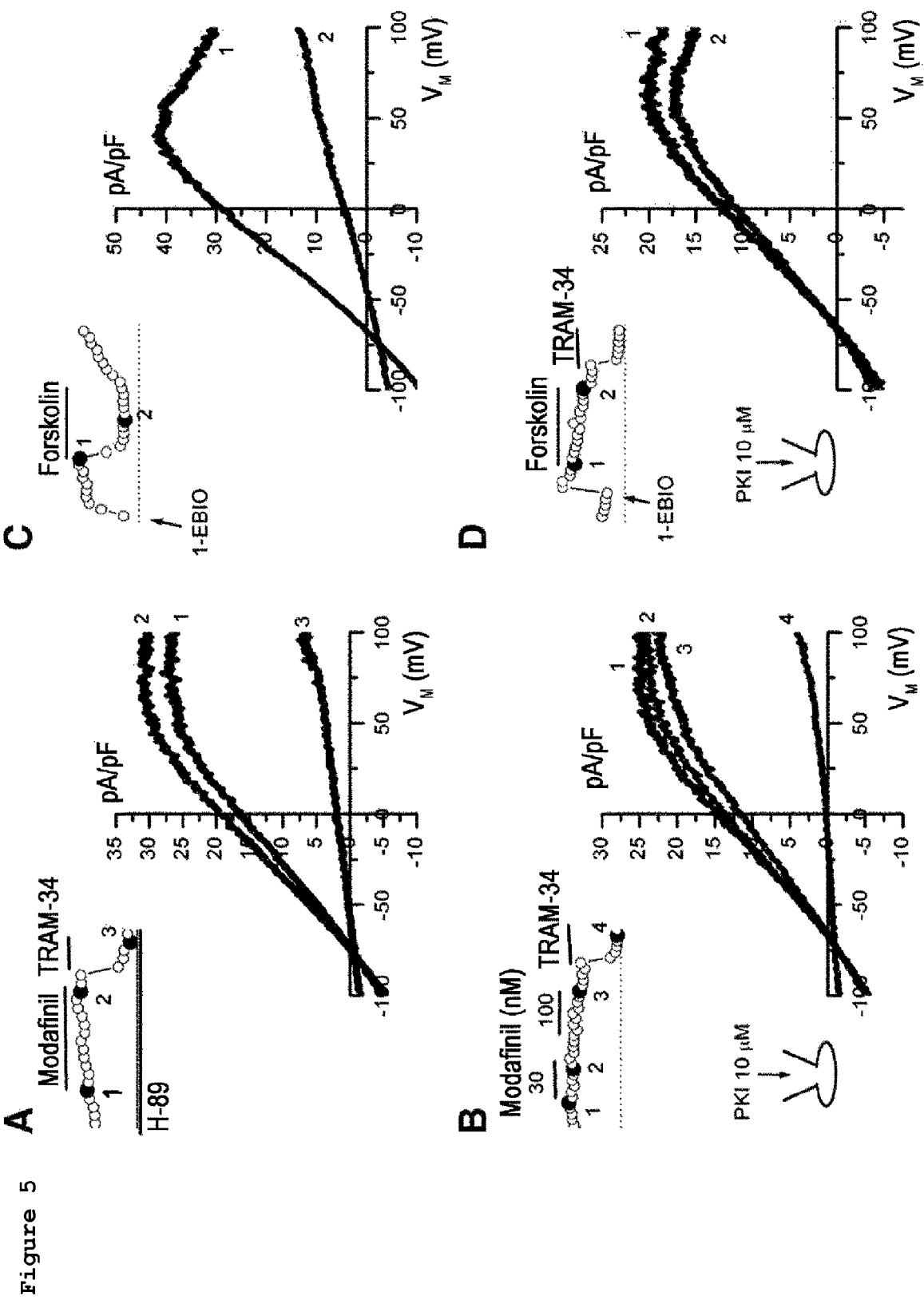
FIG. 5 is a diagram illustrating the role of PKA in modafinil-induced KCa3.1 current inhibition. KCa3.1 currents were activated by loading Ca2+ (1 µM) and applying 1-EBIO (100 µM). Data points were obtained at 50 mV during repetitive ramps (left upper traces), and I-V curves obtained at the points marked in upper traces are shown in right lower traces.
Figure 6:
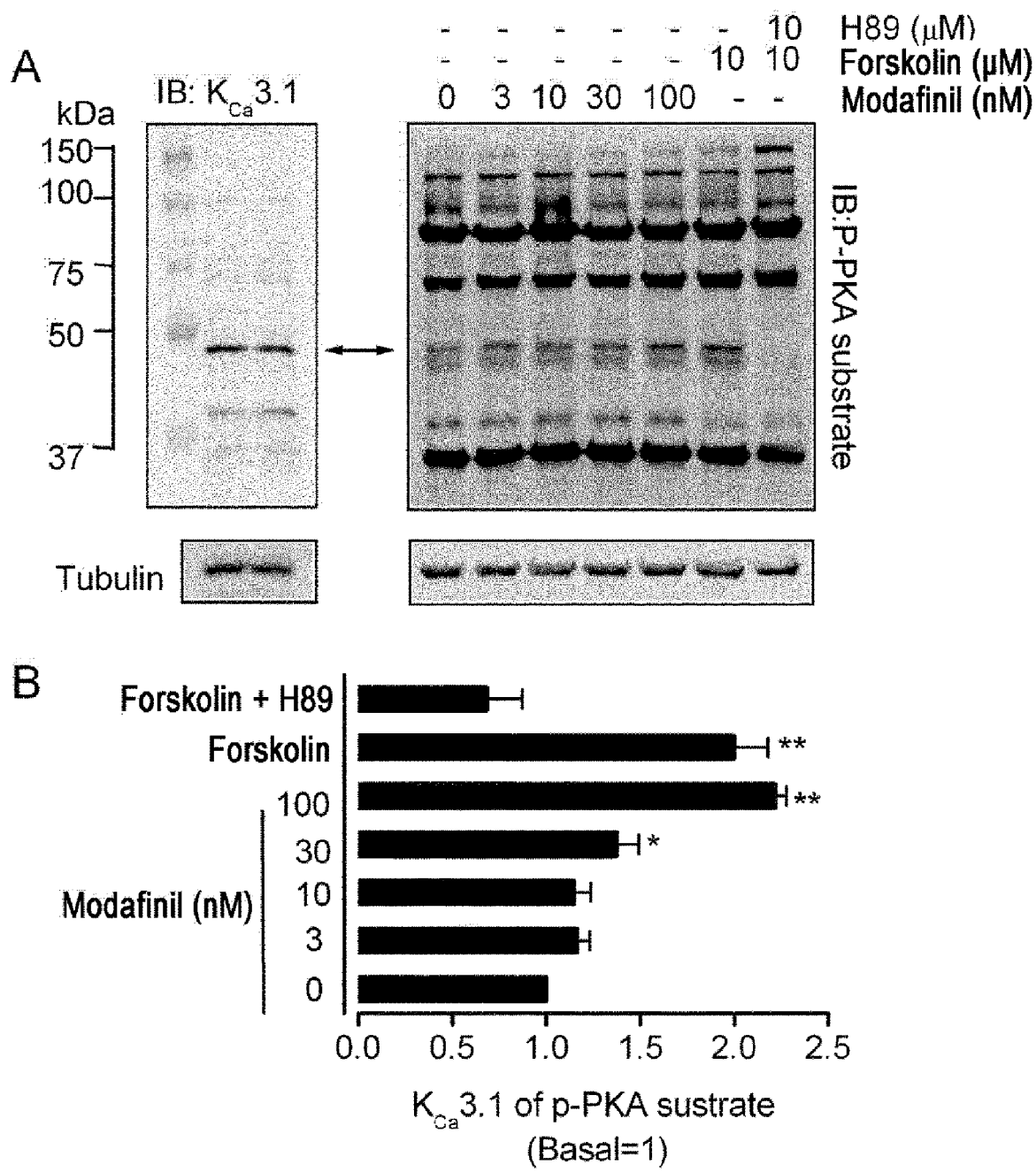
FIG. 6 is a diagram illustrating modafinil-induced KCa3.1 channel phosphorylation. Modafinil induces KCa3.1 channel phosphorylation in NIH-3T3 cells.
Figure 7:
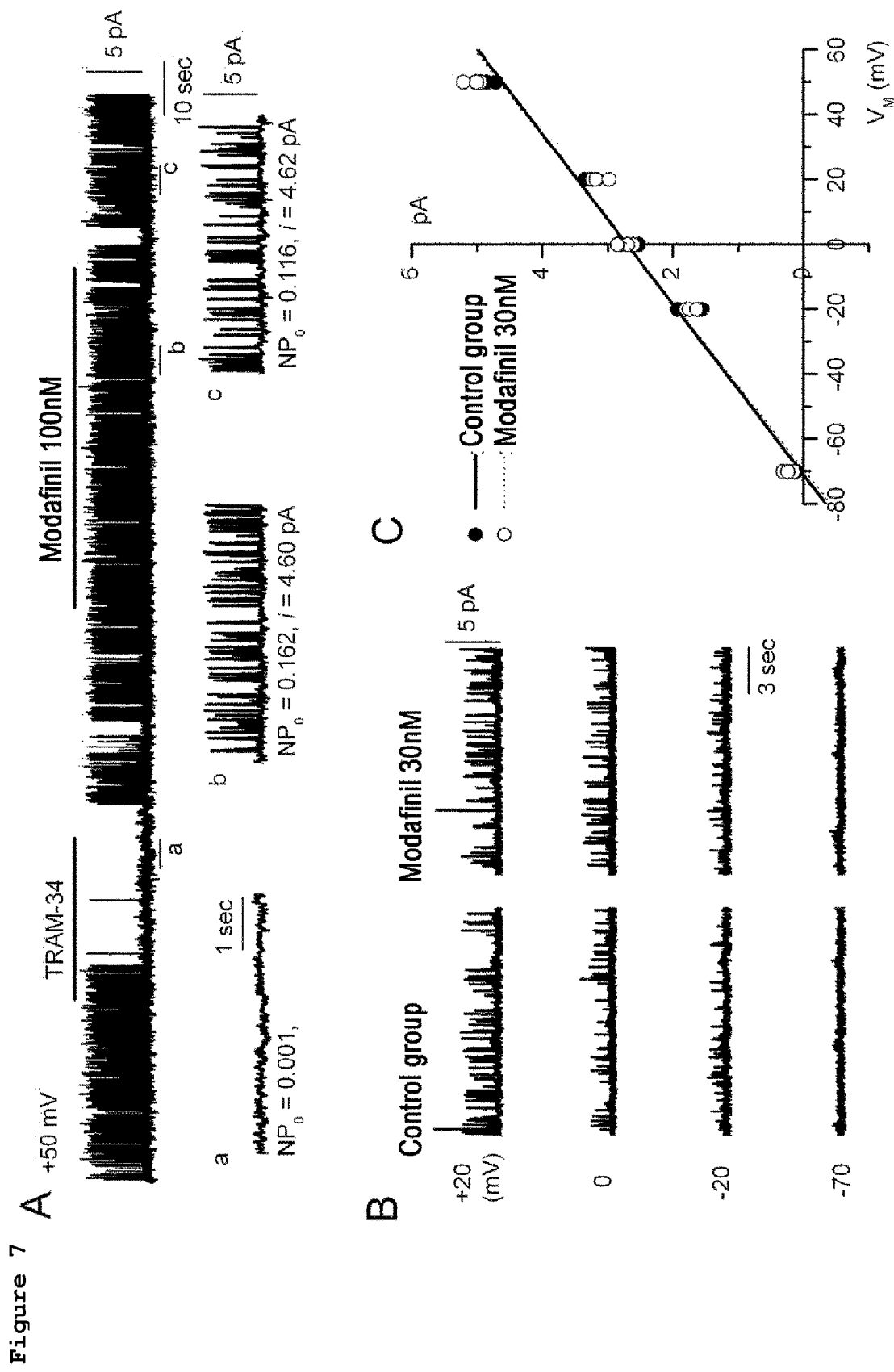
FIG. 7 is a diagram illustrating the effect of modafinil on KCa3.1 channel activity in NIH-3T3 cells.
Figure 10:
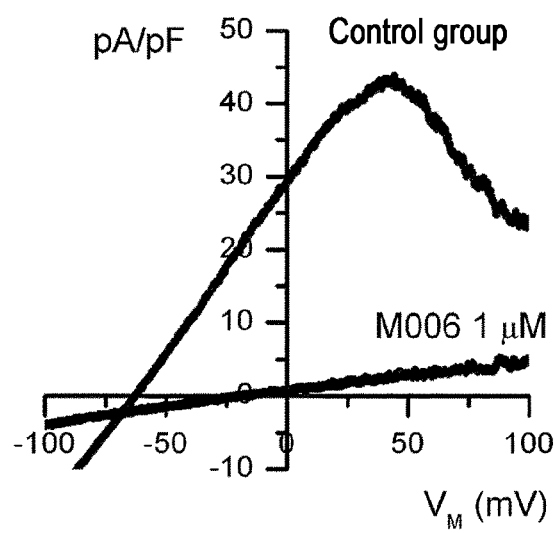
FIG. 10 is a drawing illustrating the effect of modafinil derivatives (M006, M008, M015, M020) on the KCa3.1 channel current. The effect of the derivatives is very similar to that of modafinil, as the KCa3.1 channel currents were inhibited.
Figure 10:
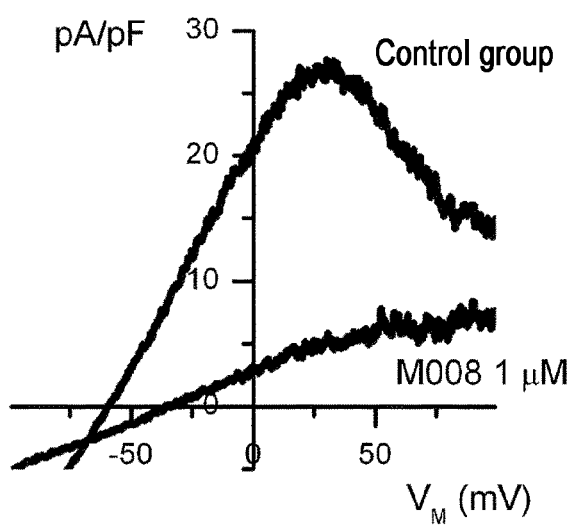
Figure 10:
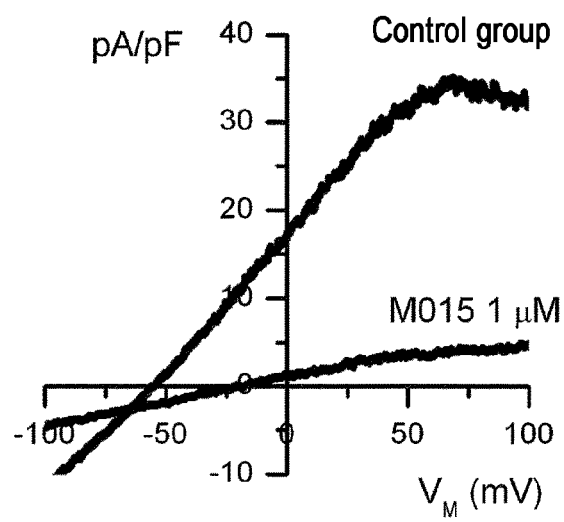
Figure 10:
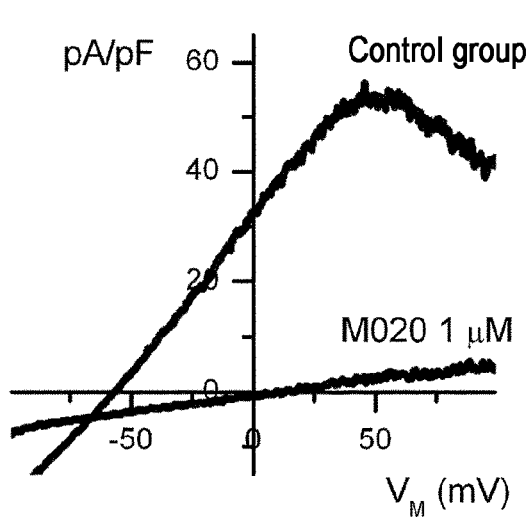

According to the embodiment of the present invention, application of modafinil showed an effect of inhibiting KCa3.1 currents (FIG. 4), such inhibitory effect of modafinil on KCa3.1 currents were inhibited by protein kinase A (PKA) inhibitor H89 and protein kinase inhibitor (PKI), and PKA activator forskolin inhibited KCa3.1 currents like modafinil and such effect of forskolin was inhibited by PKA inhibitor (FIG. 5). The results show possibility of modafinil to activate PKA. And modafinil increased intracellular cAMP concentration (FIG. 2), and phosphorylated KCa3.1 channel protein (FIG. 6). Since modafinil does not have any effect on the activity of KCa3.1 channel (single-channel conductivity and current level), it was verified that the inhibitory effect of modafinil on KCa3.1 currents was not the result of directly inhibiting KCa3.1 channel (FIG. 7). Therefore, the present inventors were able to infer the action mechanism of modafinil of inhibiting KCa3.1 channel by increasing intracellular cAMP concentration, activating PKA, and phosphorylating KCa3.1 channel. In addition, compounds having the structures of Chemical Formulae 2 to 5 showed a similar effect of increasing intracellular cAMP and inhibiting KCa3.1 current as that of modafinil (FIG. 8 and FIG. 10).

The pharmaceutical composition of the present invention may further include pharmaceutically acceptable carriers. The phrase "pharmaceutically acceptable" of the present invention is as defined above, and available carriers are as described above.

Another aspect of the present invention provides a method of preventing or treating KCa3.1 channel-mediated diseases comprising administering of the pharmaceutical composition to an individual in need.

The term "individual" of the present invention refers to any animal, including human, who has or may have a KCa3.1 channel-mediated disease, and administering the pharmaceutical composition of the present invention to the individual may prevent or treat the KCa3.1 channel-mediated disease effectively. The pharmaceutical composition of the present invention may be administered in combination with an existing treatment of KCa3.1 channel-mediated diseases.

The term "administering" of the present invention is used in the same manner as described above.

Meanwhile, the pharmaceutical composition of the present invention is administered in a pharmaceutically effective amount, and the phrase "pharmaceutically effective amount" is also the same as described above.

Another aspect of the invention provides a health functional food composition for the prevention or improvement of KCa3.1 channel-mediated diseases comprising modafinil of the Chemical Formula 1 or modafinil derivatives of the Chemical Formulae 2 to 5, or sitologically acceptable salts thereof.

The definition and types of health functional food are the same as described above.

Hereinafter, the features and effect of the present invention will be described in more detail based on embodiments. Meanwhile, the scope of the present invention is not limited by the embodiments but the present invention may be implemented in accordance with the embodiments.

Embodiment 1: Cell Isolation and Culture

Single smooth muscle cells (SMCs) were used to examine the effect of modafinil on vascular diseases. Single smooth muscle cells were separated from an aorta of the mouse. Three to four-month-old mice of either gender were anaesthetized with pentobarbital sodium (50 mg/kg weight) and sacrificed by cervical dislocation. Thoracic aortas were dissected out in Ca2+-free external solution and dissociated by incubation in papain (1 mg/ml) for 5 min followed by incubation in collagenase (1.5 mg/ml), bovine serum albumin (BSA; 2 mg/ml) and dithiothreitol (1 mg/ml) for 10 to 20 min in Ca2+-free external solution at 37° C. Segments were then transferred to fresh Ca2+-free external solution, and single mouse SMCs were dispersed with gentle agitation using a glass pipette. Mouse aortic SMCs were cultivated in Dulbecco's Modified Eagle Medium (DMEM) containing 10% fetal bovine serum (FBS) plus 1% minimum essential amino acids (Life Technologies). Cell culture was maintained at 37° C. in fully humidified air with 5% CO2.

Meanwhile, NIH-3T3 fibroblasts were used to verify the effect on KCa3.1 mediated diseases. NIH-3T3 fibroblasts (CRL-2795; American Type Culture Collection, VA, USA) were maintained in the following manner. Cells were cultivated as a monolayer in Dulbecco's Modified Eagle Medium (DMEM, Hyclone, Logan, Utah, USA) added with 10% fetal bovine serum (FBS), 100 units/ml penicillin, and 100 μg/ml streptomycin. All cells were maintained at 37° C. in humidified condition under 5% CO2. Media were changed twice weekly, and cultures were passaged at a dilution of 1:5 weekly. The medium was then removed and replaced with fresh medium, and the cells were maintained for the time periods indicated.

Embodiment 2: Measurement of Intracellular cAMP 2.1. Mouse Aortic Smooth Muscle Cells Cultured mouse aortic SMCs were incubated with modafinil for 3 minutes within incomplete media. The concentration of cAMP (adenosine 3",5"-cyclic monophosphate) from lysate was determined in each sample using a Parameter cAMP assay kit (R&D Systems) according to the manufacturer's instructions.

The present inventors examined the increasing of cAMP concentration due to modafinil. As illustrated in FIG. 1, when the cultured mouse aortic SMCs were exposed to modafinil for 3 minutes, intracellular cAMP concentration increased in a concentration-dependent manner. The result showed the mechanism same as that of an existing treatment for pulmonary hypertension, iloprost, and implied the possibility of modafinil to treat vascular diseases.

2.2. NIH-3T3 Fibroblasts

NIH-3T3 fibroblasts were incubated with modafinil for 3 minutes within incomplete media. The concentration of cAMP (adenosine 3',5'-cyclic monophosphate) from lysate was determined in each sample using a Parameter cAMP assay kit (R&D systems) according to the manufacturer's instructions.

PKA is activated by cAMP and phosphorylates intracellular proteins such as KCa3.1 protein. Therefore, the present inventors examined the increasing of cAMP concentration due to modafinil.

As a result, illustrated in FIG. 2, when NIH-3T3 cells were exposed to modafinil for 3 minutes, intracellular cAMP concentration increased in a concentration-dependent manner.

Embodiment 3: Contraction Measurement on Isolated Vascular Rings

Experimental animals were used to examine the effect of modafinil on relaxation of contracted blood vessels. Five to six-month-old mice or rats were anaesthetized by an intraperitoneal injection of pentobarbital sodium (50 mg/kg, weight). The mouse thoracic aorta and rat pulmonary artery were dissected out and cut into rings of about 3 mm. Mechanical responses were recorded from the ring segments using a home-made myograph. Each ring was threaded with two strands of tungsten wire (120 μm in diameter). One wire was anchored in the organ bath chamber (1 ml) and the other was connected to a mechano-transducer (Grass, FT-03) mounted on a three dimensional manipulator. The muscle chamber was perfused at a flow rate of 2.5 ml/minute with oxygenated (95% O2/5% CO2) Krebs/Ringer bicarbonate solution with a peristaltic pump. The composition (unit: mM) of the Krebs solution was as follows: NaCl 118.3, KCl 4.7, MgCl2 1.2, KH2PO4 1.22, CaCl2 2.5, NaHCO3 25.0, glucose 11.1, pH 7.4. Endothelial cells were removed by gentle rubbing with a cotton ball and NO production in endothelial cells was inhibited by pretreating with NG-nitro-1-arginine methyl ester (l-NAME). Rings were pre-contracted with 0.1 μM norepinephrine or 30 mM K+.

Since increase in intracellular cAMP in vascular smooth muscle cells activates PKA and phosphorylates myosin light chain active enzyme to relax vascular smooth muscles, the present inventors examined whether modafinil relaxes vascular smooth muscles. Mouse aortic rings or rat pulmonary arterial rings were contracted by norepinephrine (0.1 μM). When the contraction reached a steady-state, modafinil was applied. With the application, the contracted mouse aortic ring (FIGS. 3A and 3B) or rat pulmonary arterial ring (FIGS. 3C and 3D) was relaxed in a concentration-dependent manner. When the concentration-dependent reaction curve was fitted to Hill's equation, the IC50 of modafinil for mouse aortic rings and rat pulmonary arterial rings was determined to be 11.9±0.3 nM and 10.1±0.1 nM, respectively. When rat pulmonary artery was contracted by K+ (30 mM) of a high concentration, modafinil relaxed the contracted artery in a concentration-dependent manner (FIG. 3E). When the concentration-dependent reaction of rat pulmonary artery was fitted to Hill's equation, the IC50 of modafinil was determined to be 10.5±0.4 nM (FIG. 3F).

Embodiment 4: Electrophysiological Analysis 4.1. Method of Electrophysiology Analysis Electrophysiological analysis was performed according to the methods reported by Nilius and the like [Nilius et al., 1993, Pflugers Arch., 424(3-4): 285-293]. The patch-clamp technique was used in the whole-cell and excised patch configurations at room temperature. Whole-cell currents were measured using ruptured patches. Currents were monitored using an appropriate amplifier (EPC-10, HEKA, Lambrecht, Germany). In the whole cell experiment, we applied a voltage ramp from −100 mV to +100 mV with a 10 sec interval (650 ms duration) or voltage steps from a holding potential of −60 mV to potentials ranging from −100 mV to +100 mV in 20 mV increments (1 sec duration) with a 5 sec interval. Currents were recorded at a sampling rate of 1-4 kHz. Inside-out voltage clamps were performed using glass electrodes of tip resistance of 8-10 MΩ. Data were filtered at 1 KHz and stored in a computer for analysis using standard software (Axoscope 9.0, Axon Instruments, Foster City, Calif., USA). For some experiments, channel activity was expressed as the product of the number of channels times open probability (NPo), where NPo=Σ[(open time×number of open channels)/Total time of record].

The standard external solution contains the following substance within NaOH solution of pH 7.4; 150 mM NaCl, 6 mM KCl, 1.5 mM CaCl2, 1 mM MgCl2, 10 mM HEPES, and 10 mM glucoses. The osmolarity of this solution, as determined by an osmometer (Fiske, Norwood, Mass., USA), was 320±5 mOsm. In the inside-out mode, the bath solution contains 150 mM KCl, 0.5 mM MgCl2, 10 mM HEPES within KOH solution of pH 7.2, and the pipette solution contains 150 mM NaCl, 6 mM KCl, 1 mM MgCl2, 10 mM HEPES, 10 mM glucoses, 5 mM EGTA within NaOH solution of pH 7.4. Free Ca2+ concentrations in the pipette or bath solutions were adjusted to 1 μM by adding appropriate amounts of Ca2+ (calculated using CaBuf software; G. Droogmans, Leuven, ftp://ftp.cc.kuleuven.ac.be/pub/droogmans/cabuf.zip) in the presence of 5 mM EGTA.

KCa3.1 currents were activated by adding 1-ethyl-2-benzimidazolinone (1-EBIO, 100 μM) to the external solution and loading 1 μM Ca2+ via patch pipette in whole-cell clamped NIH-3T3 fibroblasts.

4.2. Inhibition of KCa3.1 Current by Modafinil

When the cell was loaded with 1 μM Ca2+ via the patch pipette and exposed to 1-EBIO, outward currents developed slowly as shown in FIG. 1. The current-voltage curve by ramp or step pulses was linear at negative potentials to 50 mV and bent toward an abscissa at positive potentials to 50 mV. The currents were inhibited by the specific KCa3.1 channel blocker TRAM-34 (FIG. 4A). These results suggest that the activated currents are KCa3.1 currents.

The present inventors then examined the effect of modafinil on KCa3.1 currents (FIG. 4B to 4D). Modafinil inhibited KCa3.1 currents in a concentration-dependent manner. When the current inhibition was fitted for each modafinil concentration with Hill's equation, the concentration required for half-maximal inhibition (IC50) of modafinil for the current inhibition was determined to be 6.8±0.7 nM, and the concentration of modafinil for maximal inhibition was 100.0±5.7 nM. Such results show that modafinil is very sensitive in inhibiting KCa3.1 currents.

4.3. PKA Inhibitors Block the Inhibitory Effect of Modafinil on KCa3.1 Currents KCa3.1 channels were reported to be inhibited by PKA-induced phosphorylation of the channel protein [Neylon C. B. et al., 2004, Pflugers Arch., 448(6): 613-620]. This suggests that modafinil might inhibit KCa3.1 currents by activating PKA. Thus, the inventors determined whether PKA inhibition by the PKA inhibitors H89 and PKI14-22 blocks the inhibitory effect of modafinil on KCa3.1 currents, and indicated the results in FIGS. 5A and 5B.

KCa3.1 currents were activated in cells pretreated by H89 (10 μM) and modafinil was then applied to the cells by adding it in the external solution. The activated KCa3.1 currents, which reached a steady state, were not inhibited by modafinil in cells pretreated by H89 (FIG. 5A). In addition, when PKI14-22 (10 μM) was applied to cells by adding it in the pipette solution, KCa3.1 currents were not affected by modafinil (FIG. 5B).

Furthermore, the inventors examined whether the PKA activator forskolin inhibits KCa3.1 currents. When the activated KCa3.1 currents reached a steady state, forskolin (10 μM) was added in the external solution; the KCa3.1 currents subsequently decreased by the application (FIG. 5C). In contrast, when PKI14-22 (10 μM) was applied to the cell by adding it to the pipette solution, the KCa3.1 currents were not affected by forskolin (FIG. 5D). These results suggest that modafinil-induced inhibition of KCa3.1 currents is via a PKA-mediated event.

Embodiment 5: Western Blotting Analysis

After the treatment, cells were washed once in ice-cold phosphate buffered saline (PBS) and lysed in protein extraction buffer containing protease inhibitor cocktail. Protein concentration in the supernatant was determined by Bradford protein assay. For Western blot analysis, 30 μg of protein was subjected to SDS-PAGE, and proteins were then transferred to a nitrocellulose membrane. Membranes were blocked for 1 hour with TBST (10 mM Tris-HCl, 150 mM NaCl, and 1% (v/v) Tween-20, pH 7.6) containing 5% bovine serum albumin (BSA) at room temperature. The blots were incubated for 3 hours with rabbit anti-P-PKA substrate antibody followed by incubation with horseradish peroxidase-conjugated secondary antibodies for 1 hour. Bands were visualized by chemiluminescence. Data collection and processing were performed using a luminescent image analyzer LAS-3000 and IMAGE GAUSE software (Fuji Film, Japan).

As mentioned in Embodiment 2, PKA is activated by cAMP and phosphorylates intracellular proteins such as KCa3.1 protein. Therefore, the present embodiment examined whether modafinil increases cAMP and phosphorylates KCa3.1 protein. As a result illustrated in FIG. 4, modafinil increased KCa3.1 phosphorylation in a concentration-dependent manner, and the phosphorylation was inhibited by H89.

The presence of KCa3.1 channels was confirmed using Western blotting (FIG. 6A left panel). KCa3.1 channel phosphorylation was shown in the resting state, and channel phosphorylation was increased by the treatment of modafinil or forskolin for 5 min (FIG. 6A right panel). The channel phosphorylation in the resting state and by forskolin was completely abolished by h89.

These results suggest that modafinil activates PKA by increasing cAMP to phosphorylate target proteins such as the KCa3.1 channels and thereby inhibits KCa3.1 channel.

The above experimental results indicate that modafinil increases intracellular cAMP, activates PKA, and PKA phosphorylates KCa3.1 channels to inhibit KCa3.1 currents. In addition, the results suggest that modafinil phosphorylates KCa3.1 channel protein in a very low concentration of nanomolar unit to inhibit the ion pathway.

Embodiment 6: Independence Verification of Modafinil and KCa3.1 Channel Activities Since KCa3.1 channels are activated by intracellular Ca2+, modafinil might inhibit KCa3.1 currents by decreasing Ca2+ sensitivity. Thus, the present inventors examined whether modafinil modulates KCa3.1 currents by changing Ca2+ sensitivity. Modafinil (30 nM) did not affect EC50 of Ca2+ on KCa3.1 currents.

To further show that KCa3.1 current inhibition by modafinil is not the result of a direct interaction between KCa3.1 channels and modafinil, the present inventors examined whether modafinil affects the activity of KCa3.1 channels. In inside-out patches, KCa3.1 channels were activated by clamping Ca2+ concentration of the bath solution to 1 μM and applying 1-EBIO. The holding potential was then changed from −70 to 50 mV (FIG. 7). The single channel currents were inhibited by TRAM-34. This suggests that the activated currents were through KCa3.1 channels (FIG. 6A). The present inventors then applied modafinil (30 or 100 nM) to the bath solution. Modafinil did not change single channel activity of KCa3.1 channels. The open probability was also not changed by modafinil (FIGS. 7A and 7B). A linear fit of the data between 50 to −70 mV yielded a slope conductance of 38.1 pS in the control group and 39.4 pS in the presence group of modafinil (FIG. 7C). The single channel conductance recorded in the control condition was very close to that in the presence group of modafinil (30 μM), indicating that the conductance of the single channel was not changed by modafinil.

Embodiment 7: Effect of Modafinil Derivatives

7.1. Vascular Diseases

Cultured mouse vascular smooth muscle cells and rat pulmonary vascular ring of the derivatives of modafinil were used using the same methods of Embodiments 2 and 3 to observe the effect on the intracellular cAMP concentration and norepinephrine-pre-contracted blood vessels. 4 derivatives of M006 of Chemical Formula 2, M008 of Chemical Formula 3, M015 of Chemical Formula and M020 of Chemical Formula 5 of synthesized modafinil derivatives were found to show the similar effects as the effects of modafinil observed in the Embodiments. Increase in the intracellular cAMP concentration due to the derivatives of modafinil M006, M008, M015 and M020 is illustrated in FIG. 8 and the inhibitory effect on muscle contraction of the derivatives of thereof is illustrated in FIG. 8.

Compared to the control group, treating with derivatives of modafinil increased the intracellular cAMP concentration of 1 μM to about 2 times, 100 μM to about 5 times or more (FIG. 8). Also, the blood vessel relaxation effect in the pre-contracted rat pulmonary was observed to be the similar level as when treated with modafinil (FIG. 9). These results suggest the treatment effect of derivatives of the present invention on vascular diseases by increasing intracellular cAMP similar to that of modafinil.

7.2. KCa3.1 Channel-Mediated Diseases

The effects of modafinil derivatives on the intracellular cAMP concentration in the cultured NIH-3T3 fibroblasts and KCa3.1 currents were observed in the same manner as Embodiments 4 and 5.

4 derivatives of M006 of Chemical Formula 2, M008 of Chemical Formula 3, M015 of Chemical Formula 4 and M020 of Chemical Formula 5 of synthesized modafinil derivatives were observed to show similar effects as that of modafinil in the Embodiments.

FIG. 7 illustrates increase in the intracellular cAMP concentration by the derivatives of modafinil, M006, M008, M015 and M020 and FIG. 8 illustrates the inhibitory effect of the derivatives on KCa3.1 currents and muscle contraction. Compared to the control group, treating with modafinil derivatives increased the intracellular cAMP concentration of 1 μM to about 2 times, 100 μM to about 5 times or more (FIG. 7). Also, the inhibitory effect on KCa3.1 currents showed in similar level when treated with modafinil (FIG. 10). The derivatives of the present invention not only increased the intracellular cAMP similarly to modafinil, but also inhibited KCa3.1 channels, thus the result suggests the therapeutic effect of KCa3.1 mediated diseases.

Comparative Example 1

Comparison of Intracellular cAMP Increase and Blood Vessel Contraction Inhibition Effect Between Iloprost of an Existing Pulmonary Hypertension Treatment and the Compounds of the Present Invention The present inventors compared the effect of iloprost which is used to treat pulmonary hypertension with modafinil, in light of intracellular cAMP concentration increase and blood vessel contraction inhibition effect. Iloprost also inhibited rat pulmonary arterial contraction by norepinephrine (1 μM); the IC50 was 39.4±5.1 nM. Intracellular cAMP concentration was increased by 1 μM of iloprost and the degree of increase was similar to that of 1 μM of modafinil. These results suggest that modafinil has at least as potentiality as iloprost in activating cAMP/PKA, thereby inhibiting vascular smooth muscle (VSM) contraction (FIG. 11). Since iloprost is now commercially available as a treatment for pulmonary arterial hypertension, modafinil having the same mechanism action as iloprost may also be possible to be used as a treatment for pulmonary arterial hypertension.

Comparative Example 2

Comparison Between the Effect of Existing PKA Activator Forskolin and that of Compounds of the Present Invention on Intracellular cAMP Increase, KCa3.1 Current and KCa3.1 Channel Phosphorylation The present inventors compared the effects of modafinil and PKA activator forskolin on intracellular cAMP concentration increase, KCa3.1 current and KCa3.1 channel phosphorylation. The concentration of cAMP was measured after treating NIH-3T3 cell with the medication. AS the result shown in FIG. 2B, treating the cell with 1 μM of modafinil showed 2 times the concentration of cAMP compared to treating the cell with 10 μM of forskolin. Further, whether the medications inhibit KCa3.1 currents was examined. When the activated KCa3.1 currents reached a steady state, forskolin (10 μM) was added in the external solution; the KCa3.1 currents subsequently decreased by the application (FIG. 5C). In contrast, when PKI14-22 (10 μM) was applied to the cell by adding it to the pipette solution, the KCa3.1 currents were not affected by forskolin (FIG. 5D). These results suggest that modafinil-induced inhibition of KCa3.1 currents is accomplished via a PKA-mediated event.

Finally, the presence of KCa3.1 channels was confirmed using Western blotting (FIG. 6A left panel). KCa3.1 channel phosphorylation was shown in the resting state, and channel phosphorylation was increased by the treatment of modafinil or forskolin for 5 min (FIG. 5A right panel). The channel phosphorylation in the resting state and by forskolin was completely abolished by H89. These results suggest that modafinil activates PKA by increasing cAMP to phosphorylate target proteins such as KCa3.1 channels and thereby inhibits KCa3.1 channel.

Embodiment 8: The General Synthetic Example of Modafinil Derivatives

Dissolve the carboxylic acid compound (0.77 mmol) represented by the following Chemical Formula 6 or 7 in dimethylformamide (DMF, 40 ml) and add each of HOBt[208 mg, 1.54 mmol, (1-hydroxybenzotriazole)] and EDC[295 mg, 1.54 mmol, (ethyl(dimethylaminopropyl)carbodiimide and stir at room temperature for 30 minutes. Add amine compound (0.77 mmol) in the reaction solution and conduct the reaction at room temperature for 1 hour, cleanse with ethylacetate (100 ml) and brine (100 ml), separate and dry the organic layer, remove the solvent under the reduced pressure and purify the residue by the chromatography to obtain the target compound of modafinil derivative.

[Chemical Formula 6]

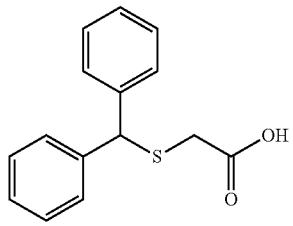

[Chemical Formula 7]

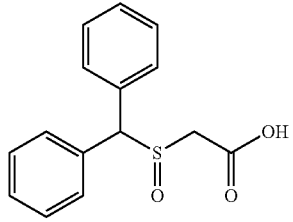

Preparation Example 1

2-(benzhydryl thio)-N-((tetrahydrofuran-2-yl)methyl)acetamide (M006)

With the compound of Chemical Formula 6 in the Embodiment 8 as the starting material, tetrahydro-perfuryl amines was used for amine compounds to perform the reaction by the same method as the Embodiment 8 to produce the target compound and the characteristics are as follows.

White solid. mp 117.8; Rf=0.3 (ethyl acetate/n-hexane=1: 1, v/v); IRmax (CHCl3, KBr) 3304, 3060, 3027, 2926, 2870, 1651, 1531, 1494, 1450, 1384, 1304, 1078, 1030, 922, 750, 702, 629, 587, 507 cm-1; 1H NMR (250 MHz, CDCl$_3$) δ=7.43-7.20 (m, 10H), 6.99 (s, 1H), 5.20 (s, 1H), 3.99-3.75 (m, 3H), 3.58-3.52 (m, 1H), 3.19-3.09 (m, 3H), 2.02-1.87 (m, 4H); 13C-NMR (63 MHz, CDCl3) δ=168.5, 140.3, 128.8, 128.4, 127.6, 68.2, 54.8, 43.5, 36.1, 29.8, 25.9; LC-MS (ESI+) m/z 364—[M+Na].

Preparation Example 2

2-(benzhydryl thio)-N-phenylacetamide (M008)

With the compound of Chemical Formula 6 in the Embodiment 8 as the starting material, aniline was used for amine compound to perform the reaction by the same method as the Embodiment 8 to produce the target compound, and the characteristics are as follows.

White solid. mp 98.9; Rf=0.43 (ethyl acetate/n-hexane=1: 2, v/v); IRmax (CHCl3, KBr) 3301, 3060, 3019, 2913, 1659, 1601, 1540, 1495, 1442, 1319, 1242, 1074, 1029, 747, 690, 625, 584, 498 cm-1; 1H NMR (250 MHz, CDCl3) δ=8.45 (s, 1H), 7.49-7.08 (m, 15H), 5.19 (s, 1H), 3.23 (s, 2H); 13C-NMR (63 MHz, CDCl$_3$) δ=166.7, 140.3, 137.7, 129.2, 129.0, 128.5, 127.9, 124.8, 119.9, 54.3, 37.2; LC-MS (ESI+) m/z 356—[M+Na].

Preparation Example 3

2-(benzhydryl sulfinyl)-N-methylacetamide (M015)

With the compound of Chemical Formula 7 in the Embodiment 8 as the starting material, methane amine was used for amine compound to perform the reaction by the same method as the Embodiment 8 to produce the target compound, and the characteristics are as follows.

White liquid. Rf=0.08 (ethyl acetate/n-hexane=2:1, v/v); IRmax (CHCl3, KBr) 2961, 2926, 1736, 1494, 1451, 1282, 1117, 1053, 1031, 967, 753, 702 cm-1; 1H NMR (250 MHz, CDCl$_3$) δ=7.50-7.34 (m, 10H), 7.09 (s, 1H), 5.21 (s, 1H), 3.43 (d, J=13.90 Hz, 1H), 3.15 (d, J=13.90 Hz, 1H), 2.79 (d, J=4.74 Hz, 3H); 13C-NMR (63 MHz, CDCl$_3$) δ=164.9, 135.0, 129.7, 129.6, 129.0, 128.8, 72.3, 52.7, 26.6; LC-MS (ESI+) m/z 310—[M+Na].

Preparation Example 4

2-(benzhydryl sulfinyl)-N-((tetrahydrofuran-2-yl) methyl) acetamide (M020)

With the compound of Chemical Formula 7 in the Embodiment 8 as the starting material, tetrahydro-perfuryl amines was used for amine compound to perform the reaction by the same method as the Embodiment 8 to produce the target compound, and the characteristics are as follows.

White liquid. Rf=0.1 (ethyl acetate/n-hexane=2:1, v/v); IRmax (CHCl3, KBr) 3287, 3064, 2926, 2871, 2243, 1738, 1667, 1556, 1495, 1451, 1383, 1304, 1257, 1136, 1080, 1031, 911, 732, 703, 646, 595, 498 cm-1; 1H NMR (250 MHz, CDCl3) δ=7.53-7.27 (m, 1H), 5.28 (s, 1H), 4.03-3.99 (m, 1H), 3.88-3.82 (m, 1H), 3.76 (t, J=6.79 Hz, 1H), 3.49-3.42 (m, 2H), 3.19-3.10 (m, 2H), 2.04-1.86 (m, 4H); 13C-NMR (63 MHz, CDCl3) 164.5, 135.2, 129.4, 128.9, 128.7, 71.3, 68.2, 52.9, 52.6, 43.6, 28.8, 25.9; LC-MS (ESI+) m/z 380—[M+Na].

The invention claimed is:

1. A method of treating KCa3.1 channel-mediated disease comprising administering the composition comprising modafinil or derivatives of modafinil having below Chemical Formulas 2 to 5, or pharmaceutically acceptable salts thereof to an individual in need thereof,
wherein the KCa3.1 channel-mediated disease is any one selected from the group consisting of sickle cell anemia;
immune diseases comprising acute immune response or auto-immune diseases;
vascular diseases comprising hypertension, ischemic coronary artery disease, arteriosclerosis, peripheral arterial occlusion, restenosis, atherosclerosis or pulmonary hypertension;
cancers comprising prostate cancer or pancreatic cancer; and
secretory diarrhea

[Chemical Formula 2]

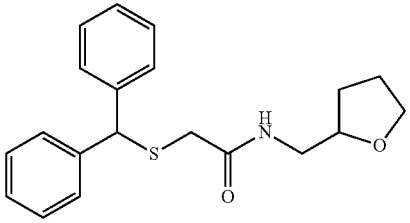

[Chemical Formula 3]

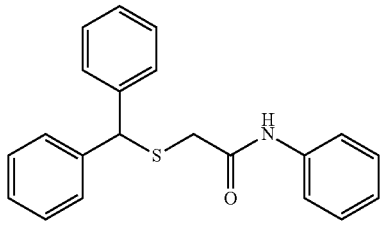

[Chemical Formula 4]

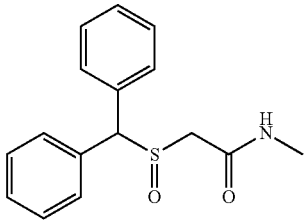

[Chemical Formula 5]

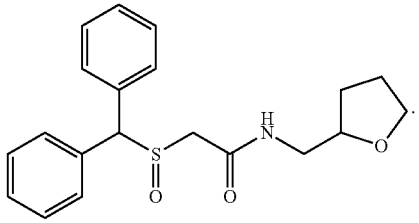

2. The method of claim 1, the composition further comprising a pharmaceutically acceptable carrier.

3. The method of claim 1, wherein the composition relaxes vascular smooth muscle by increasing intracellular cAMP concentration.

4. The method of claim 1, wherein the composition inhibits KCa3.1 channel by increasing intracellular cAMP concentration.

* * * * *